United States Patent
Sauvageau et al.

(10) Patent No.: US 12,011,460 B2
(45) Date of Patent: Jun. 18, 2024

(54) EXPANSION OF NK AND DC CELLS IN VIVO MEDIATING IMMUNE RESPONSE

(71) Applicant: UNIVERSITE DE MONTREAL, Montréal (CA)

(72) Inventors: Guy Sauvageau, Montréal (CA); Sandra Cohen, Montréal (CA); Jean Roy, Ville Mont-Royal (CA); Silvy Lachance, Westmount (CA); Jean-Sébastien Delisle, Saint-Lambert (CA); Jalila Chagraoui, Montreal (CA)

(73) Assignee: UNIVERSITE DE MONTREAL, Montréal (CA)

( * ) Notice: Subject to any disclaimer, the term of this patent is extended or adjusted under 35 U.S.C. 154(b) by 809 days.

(21) Appl. No.: 16/970,473

(22) PCT Filed: Feb. 20, 2019

(86) PCT No.: PCT/CA2019/050208
§ 371 (c)(1),
(2) Date: Aug. 17, 2020

(87) PCT Pub. No.: WO2019/161494
PCT Pub. Date: Aug. 29, 2019

(65) Prior Publication Data
US 2021/0085714 A1 Mar. 25, 2021

Related U.S. Application Data

(60) Provisional application No. 62/632,733, filed on Feb. 20, 2018.

(51) Int. Cl.
| | |
|---|---|
| C07D 471/14 | (2006.01) |
| A61K 35/15 | (2015.01) |
| A61K 35/17 | (2015.01) |
| A61K 35/28 | (2015.01) |
| A61P 37/04 | (2006.01) |
| C12N 5/0783 | (2010.01) |

(52) U.S. Cl.
CPC .............. *A61K 35/17* (2013.01); *A61K 35/15* (2013.01); *A61K 35/28* (2013.01); *A61P 37/04* (2018.01); *C07D 471/14* (2013.01); *C12N 5/0646* (2013.01); *C12N 2501/999* (2013.01); *C12N 2506/1315* (2013.01)

(58) Field of Classification Search
None
See application file for complete search history.

(56) References Cited

U.S. PATENT DOCUMENTS

| | | | |
|---|---|---|---|
| 8,440,177 | B2 | 5/2013 | Gonzalez De La Pena et al. |
| 9,409,906 | B2 * | 8/2016 | Sauvageau .............. A61P 43/00 |
| 2008/0188500 | A1 | 8/2008 | Arvanitis |
| 2008/0207632 | A1 | 8/2008 | Bearss |
| 2009/0029982 | A1 | 1/2009 | Bearss |
| 2009/0062318 | A1 | 3/2009 | Gangjee |
| 2010/0210639 | A1 | 8/2010 | Collins |
| 2011/0212929 | A1 | 9/2011 | Hurley |
| 2015/0011543 | A1 | 1/2015 | Sauvageau et al. |
| 2015/0246934 | A1 | 9/2015 | Bensen |

FOREIGN PATENT DOCUMENTS

| | | |
|---|---|---|
| AU | 2018200424 | 2/2018 |
| CA | 2858069 | 6/2013 |
| CA | 3002066 | 4/2017 |
| CN | 106414445 | 2/2017 |
| JP | 2018502115 | 1/2018 |
| KR | 20080105555 | 12/2008 |
| WO | 9718297 | 5/1997 |
| WO | 2003037898 | 5/2003 |
| WO | 2011056739 | 5/2011 |
| WO | 2013110198 | 8/2013 |
| WO | 2015/161373 | 10/2015 |
| WO | 2016109661 | 7/2016 |
| WO | 20171205977 | 12/2017 |

OTHER PUBLICATIONS

Fares et al., "EPCR expression marks UM/71-expanded CD34' cord blood stem cells", Blood, 2017, vol. 129(25), pp. 3344-3351, ISSN 1528-0020.
Fares et al., "Pyrimidoindole derivatives are agonisis of human hematopoietic stem cell self-renewal". Science, Sep. 19, 2014 (Sep. 19, 2014), vol. 345(6203), pp. 1509-1512, ISSN1095-9203.
Cohen et al., "Single UM171 Expanded Cord Blood Transplant is Feasible, Safe, and Permits Transplantation of Better HLA Matched Cords with Very Low Transplant Related and Mortality". Biol Blood Marrow Transplant, Mar. 2018 (Mar. 2018), vol. 24, pp. 59 S156-SI57,ISSN 1083-8791.
Showalter, H.D. Hollis et al, "Tyrosine Kinase inhibitors. 16. 6, 5, 6-Tricyclic benzothieno[3,2-d]pyrimidines and pyrimido]5,4,-b]- and –[4,5-b]indoles as potent inhibitors of the epidermal growth factor receptor tyrosine kinase", Journal of Medicinal Chemistry, vol. 42, No. 26. 1999.
Venugopalan, et al. "Synthesis of 6,7-dimethyoxypyrimidol[4,5-b]-indoles as potential antihypertensive agents", Journal of Heterocyclic Chemistry, 1988.
Kittlemann, Matthias et al. "Microbial hydroxylation and simultaneous formation of the 4"-O-methylglucoside of the tyrosine-kinase inhibitor CGP 62706", Chimia, 1999.
Bundy, Gordon L. et al. "Synthesis of 2, 4-di-1-pyrrolidinyl-9H-pyrimido[4,5-b]indoles, including antiasthma clinical candidate PNU-142731A", Organic Process Research and Development, 2001.

(Continued)

*Primary Examiner* — Daniel C Gamett
(74) *Attorney, Agent, or Firm* — NORTON ROSE FULBRIGHT CANADA LLP

(57) ABSTRACT

It is provided a method of expanding dendritic (DC) cells and/or natural killer (NK) cells in vivo in a patient comprising the steps of producing a graft of stem and progenitor cells cultured with UM171 or analogues therefrom and expanded before being administered to the patient. The expansion or increase in dendritic (DC) cells and/or natural killer (NK) cells population in the patient results in an increase immune response reducing transplant related mortality (TRM), severe graft-versus-host disease (GVHD), relapse, and/or severe viral infections.

15 Claims, 4 Drawing Sheets

(56) References Cited

OTHER PUBLICATIONS

English Translated Abstract KR20080105555A.
Catherine M. Sawai et al, "Hematopoietic stem cells are the major source of multilineage hematopoiesis in adult animals", Immunity, vol. 45, pp. 597-609.
English Machine Translation of JP 2018-502115 A.

* cited by examiner

EXPANSION OF NK AND DC CELLS IN VIVO MEDIATING IMMUNE RESPONSE

CROSS-REFERENCE TO RELATED APPLICATIONS

The present application is a U.S. National Phase of International Application No. PCT/CA2019/050208, filed on Feb. 20, 2019, and claims benefit of U.S. Provisional Application No. 62/632,733 filed Feb. 20, 2018, the content of which is hereby incorporated by reference in its entirety.

TECHNICAL FIELD

It is provided a method of expanding dendritic (DC) cells and/or natural killer (NK) cells in vivo in a patient by transplanting a graft of stem and progenitor cells cultured with UM171 or analogues therefrom.

BACKGROUND

Immunotherapy has been considered a major breakthrough in the field of anti-cancer therapy, since this approach demonstrated its efficacy against chemotherapy refractory cancers. Although many efforts focused on antigen-targeted approaches, harnessing innate immunity to fight cancer cells has also been proposed and natural killer (NK) cells are increasingly used to design anti-cancer immunotherapy.

NK cells recognize and kill infected or transformed cells without prior sensitization. Their cytotoxicity activity against cancer cells is highly regulated by the balance between activating and inhibitory signals as well as their education in order to distinguish self and untransformed cells from cancer and infected cells. Nonetheless, cancer cells can become resistant to NK cell-mediated lysis by down-regulating ligands for NK cell activating receptors. To circumvent this resistance, NK cell stimulation is required to increase the cytotoxic functions of NK cells. Interleukin (IL)-2 and IL-15 are the most frequently used cytokines to increase NK cell lytic functions, but their use in clinics is associated with high toxicity and side effects that can dampen the efficacy of NK cell mediated cytotoxicity against cancer. Natural killer cells play a crucial role in protection against cancer relapse and infections.

NK cell functions can also be stimulated by low numbers of activated dendritic cells. Dendritic cells (DCs) are the most potent antigen-presenting cells that stimulate both innate and acquired immune responses thereby conferring resistance to infection, protective anti-tumor immunity and tolerance to self. This unique intrinsic capacity to generate a large number of high avidity effector cells, such as cytotoxic T lymphocytes and Natural killer cells, designate DCs as very good candidates for cell based therapy against various hematological malignancies including cancer, infectious diseases, allergy and autoimmune diseases. DCs can shape their functions based on their immune states, which are crucial for the balance of immunity and tolerance to preserve homeostasis. In the immune response involved in stem cell transplantation, DCs are involved in inducing immune tolerance and antitumor immunity.

Several DCs subsets have been characterized expressing different repertoires of Toll like receptors (TLR) and surface molecules and different sets of cytokines/chemokines, all of which lead to distinct and specific humoral and/or cellular immune responses. The two major subsets are the myeloid DCs (mDCs) and the plasmacytoid DCs (pDCs).

mDC and pDC respond differently to pathogenic stimuli and each subset has a specialized function in directing immune responses. While mDC produces TNF-α and IL-12 in response to microbial stimuli through TLR, pDCs, are the key effectors in innate immunity because they produce large amounts of type I interferon (IFN) in response to bacterial or viral infections. Recent observations suggest that both pDCs and mDCs are important for the induction of antitumor responses and may act synergistically to induce stronger immunological outcome.

Allogeneic hematopoietic stem cell (HSC) transplant is the best available therapy to cure patients with blood cancers. The risks of graft rejection, tumor recurrence, and tumorigenicity are still present after stem cell transplantation. Unfortunately, 40% of patients will not have a human leucocyte antigen (HLA) matched donor (related or unrelated). Cord blood (CB) is the most attractive alternative donor source of stem cells due to its unique properties, which include permissive HLA mismatches, low incidence of chronic graft-versus-host disease (GVHD) and rapid availability. However, these advantages are offset by the limited cell dose (i.e. small cords in banks), which results in delayed- or non-engraftment, increased infections, prolonged hospitalization and early mortality.

Allogeneic transplantation consists of a conditioning regimen (chemotherapy +/−radiation) followed by the infusion of stem cells (the graft) to eradicate residual cancer cells.

Bone marrow and stimulated peripheral blood stem cells are obtained from HLA matched related or volunteer unrelated donors while umbilical CB is donated at birth. Duration of neutropenia correlates directly with the risk of severe infections and transplant related mortality: it is shortest with peripheral blood (14 days), followed by bone marrow (19 days), but the longest with CB (26 days).

Allogeneic HSC transplant is associated with transplant related mortality rates up to 40%. The most common complications include acute (~50%) and chronic (~60%) GVHD. GVHD is a donor driven immune reaction against recipient, which frequently damages mucous membranes (mouth, eyes), skin, liver, lungs and intestinal tract. Further, infections are very common and graft failure (the absence of engraftment, ~10%) is caused by insufficient stem cells in the graft and/or graft destruction by the recipient's immune system. These complications are modulated by 4 key factors: i) the intensity of the conditioning regimen; ii) the type of graft infused (bone marrow, peripheral blood or CB); iii) the degree of HLA mismatch between the donor and recipient; and iv) the patient's comorbidities. GVHD is treated with high dose immunosuppressive drugs, including corticosteroids and frequently requires an average of 4-5 years of treatment. This prolonged need for immunosuppressive therapy further increases the risk of infections, secondary cancers and medication-related toxicities, all of which contribute to dramatically affect patients' quality of life.

Transplant recipients suffer from prolonged immunodeficiency. Initial T-cell recovery relies on peripheral expansion of donor memory T cells. This is later followed by maturation of donor stem cell-derived lymphoid progenitors into naïve T cells in the thymus, essential for reconstitution of a polyclonal T-cell repertoire. Until robust thymic output can be achieved, CB graft recipients have only naïve T cells (without memory cells) to fight against pathogens, explaining the increased risk of viral infections in the first months. As functional CD4$^+$ T cells are mandatory for production of mature memory B cells, the latter usually do not become completely reconstituted until 1-2 years following HSC transplant and humoral immunity is predominantly recipient-derived in the first year.

Currently, only 6% of available CB units have sufficient cell doses for adults. Therefore, double CB transplants have become routine in adults. Accessibility to transplant improves with 2 cords because minimal required TNC dose is lower at 1.5×107/kg/cord. Neutrophil engraftment is not improved but the risk of graft failure is reduced. Early after transplant, both cords are detected, but only one remains after 3 months. Increasing T lymphocyte and $CD34^+$ cell doses determine the surviving cord as each CB mounts an immune response to reject the other. This immune response is responsible for a higher incidence of severe acute GVHD and HSC destruction explaining why engraftment is delayed despite infusing a higher cell dose. Furthermore, the high cost makes double CBs prohibitive.

It would thus be highly desirable to be provided with a method of stimulating NK cells and/or dendritic cells in vivo after transplantation of a graft.

SUMMARY

It is provided a method of expanding dendritic (DC) cells, natural killer (NK) cells or a combination thereof in vivo in a patient comprising the steps of:
 a) culturing a starting population of stem and/or progenitor cells with at least one compound of formula I:

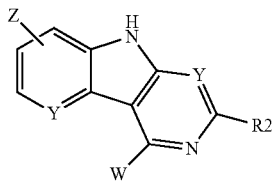

or a salt or a prodrug thereof,
wherein:
each Y is independently selected from N and CH;
Z is
 —CN
 —C(O)OR1,
 —C(O)N(R1)R3,
 —C(O)R1, or
 -heteroaryl optionally substituted with one or more RA or R4 substituents,
wherein, when (R1) and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
W is
 —CN,
 —N(R1)R3,
 —C(O)OR1,
 —C(O)N(R1)R3,
 —NR1C(O)R1,
 —NR1C(O)OR1,
 —OC(O)N(R1)R3,
 —OC(O)R1,
 —C(O)R1,
 —NR1C(O)N(R1)R3,
 —NR1S(O)$_2$R1,
 -benzyl optionally substituted with 1, 2 or 3 RA or R1 substituents,
 —X-L-(X-L)n-N(R1)R3,
 —X-L-(X-L)n-heteroaryl optionally substituted with one or more RA or R4 substituents attached on either or both the L and heteroaryl groups,
 —X-L-(X-L)n-heterocyclyl optionally substituted with one or more RA or R4 substituents attached on either or both the L and heterocyclyl groups,
 —X-L-(X-L)n-aryl optionally substituted with one or more RA or R4 substituents,
 —X-L-(X-L)$_n$-NR1RA or
 —(N(R1)-L)$_n$-N$^+$R1 R3R5 R6$^-$
wherein n is an integer equal to either 0, 1, 2, 3, 4, or 5, and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently selected from C, O, S, and NR1;
each L is independently
 —C$_{1-6}$ alkylene,
 —C$_{2-6}$ alkenylene,
 —C$_{2-6}$ alkynylene,
 —C$_{3-7}$cycloalkylene, which optionally includes one or more other heteroatom selected from N, O and S or
 —C$_{3-7}$ cycloalkenylene, which optionally includes one or more other heteroatom selected from N, O and S
wherein the alkylene, the alkenylene, the alkynylene the cycloalkylene and the cycloalkenylene groups are each independently optionally substituted with one or two R4 or RA substituent;
R1 is each independently
 —H,
 —C$_{1-6}$ alkyl,
 —C$_{2-6}$ alkenyl,
 —C$_{2-6}$ alkynyl,
 —C$_{3-7}$ cycloalkyl,
 —C$_3$— cycloalkenyl,
 —C$_{1-5}$ perfluorinated,
 -heterocyclyl,
 -aryl,
 -heteroaryl, or
 -benzyl,
wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 RA or Rd substituents;
R2 is
 —H,
 —C$_{1-6}$ alkyl, optionally substituted with one more RA substituents
 —C(O)R4,
 -L-heteroaryl optionally substituted with one or more RA or R4 substituents
 -L-heterocyclyl optionally substituted with one or more RA or R4, or
 -L-aryl optionally substituted with one or more RA or R4 substituents;
R3 is each independently
 —H,
 —C$_{1-6}$ alkyl,
 —C$_{2-6}$ alkenyl,
 —C$_{2-6}$ alkynyl,
 —C$_{3-7}$ cycloalkyl,
 —C$_{3-7}$ cycloalkenyl,
 —C$_{1-5}$ perfluorinated,

- -heterocyclyl,
- -aryl,
- -heteroaryl, or
- -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents; R4 is each independently

- —H,
- —$C_{1-6}$ alkyl,
- —$C_{2-6}$ alkenyl,
- —$C_{2-6}$ alkynyl,
- —$C_{3-7}$ cycloalkyl,
- —$C_{3-7}$ cycloalkenyl,
- —$C_{1-5}$ perfluorinated,
- -heterocyclyl,
- -aryl,
- -heteroaryl, or
- -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents; R5 is each independently

- —$C_{1-6}$ alkyl,
- —$C_{1-6}$ alkylene-$C_{2-6}$ alkenyl which optionally includes one or more other heteroatom selected from N, O and S
- —$C_{1-6}$ alkylene-$C_{2-6}$ alkynyl which optionally includes one or more other heteroatom selected from N, O and S
- -L-aryl which optionally includes one or more RA or R4 substituents
- -L-heteroaryl which optionally includes one or more RA or R4 substituents
- —$C_{1-6}$ alkylene-C(O)O—
- —$C_{1-6}$alkylene-C(O)OR1
- —$C_{1-6}$ alkylene-CN
- —$C_{1-6}$ alkylene-C(O)NR1R3, wherein R1 and R3 optionally they join together with the nitrogen atom to form a 3 to 7-membered ring which optionally includes one or more other heteroatom selected from N, O and S; or
- —$C_{1-6}$ alkylene-OH;

R6 is
- Halogen
- —OC(O)$CF_3$ or
- —OC(O)R1;

RA is each independently
- -halogen,
- —$CF_3$,
- —OR1,
- -L-OR1,
- —$OCF_3$,
- —SR1,
- —CN,
- —$NO_2$,
- —NR1 R3,
- -L-NR1 R1,
- —C(O)OR1,
- —$S(O)_2$R4
- —C(O)N(R1)R3,
- —NR1C(O)R1,
- —NR1C(O)OR1,
- —OC(O)N(R1)R3,
- —OC(O)R1,
- —C(O)R4,
- —NHC(O)N(R1)R3,
- NR1C(O)N(R1)R3, or
- —$N_3$; and Rd is each independently
- —H,
- —$C_{1-6}$ alkyl,
- —$C_{2-6}$ alkenyl,
- —$C_{2-6}$ alkynyl,
- —$C_{3-7}$ cycloalkyl,
- —$C_{3-7}$ cycloalkenyl,
- —$C_{1-5}$ perfluorinated
- -benzyl or
- -heterocyclyl;

optionally together with at least one cell expanding factor,
b) expanding the cultured population of stem and/or progenitor cells producing a graft; and
c) transplanting the graft in the patient thereby expanding DC cells, NK cells or a combination thereof in the patient.

It is also provided the use of a graft of expanded stem and/or progenitor cells cultured with at least one compound as defined herein, optionally together with at least one cell expanding factor, for expanding dendritic (DC) cells, natural killer (NK) cells or a combination thereof in vivo in a patient.

In an embodiment, the expansion of DC cells, NK cells or combination thereof stimulates an immune response in said patient.

In another embodiment, the expansion of DC cells, NK cells or combination thereof in the patient further reduces severe graft-versus-host disease (GVHD), relapse, and/or severe viral infections in said patient.

In an embodiment, the stem and/or progenitor cells are human hematopoietic stem cells (HSC).

In another embodiment, the hematopoietic stem cells are from umbilical cord blood cells, mobilized peripheral blood cells, or bone marrow cells.

In a further embodiment, the hematopoietic stem cells are from human cord blood cells.

In an embodiment, the stem and/or progenitor cells are purified for $CD34^+$, $CD38^+$, $CD90^+$, $CD45RA^+$, CD133 and/or $CD49f^+$ cells.

In another embodiment, the CD34+ cells are EPCR+ cells.

In a further embodiment, the NK cells are $CD56^+$ or $NKG2A^+$ cells.

In another embodiment, the DC cells are $CD11c^+$.

In an embodiment, the stem and/or progenitor cells are cultured with at least one cell expanding factor.

In another embodiment, the at least one cell expanding factor is interleukin-3 (IL-3), granulocyte macrophage colony-stimulating factor (GM-CSF), thrombopoieting (TPO), FMS-like tyrosine kinase 3 ligand (FLT3-L), stem cell factor (SCF), interleukin-6 (IL-6) or a combination thereof.

In a further embodiment, the stem and/or progenitor cells are further cultured with an aryl hydrocarbon receptor (AHR) antagonist.

In an embodiment, the AHR antagonist is Stem Regenin 1 (SR1) or CH223191.

In a preferred embodiment, the compound of formula I is

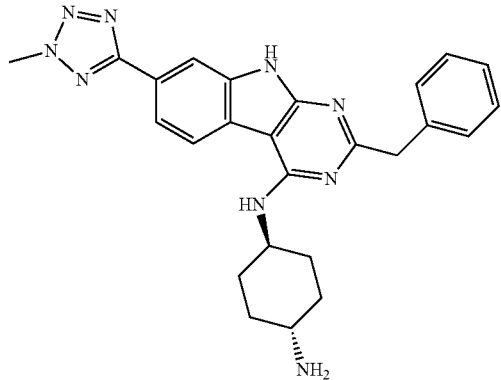 [SMILES: Cn1nnc(-c2ccc3c(c2)[nH]c2nc(Cc4ccccc4)nc(N[C@H]4CC[C@H](N)CC4)c23)n1]

or a pharmaceutically acceptable salt thereof.

In another embodiment, the compound of formula I is a hydrobromide salt of

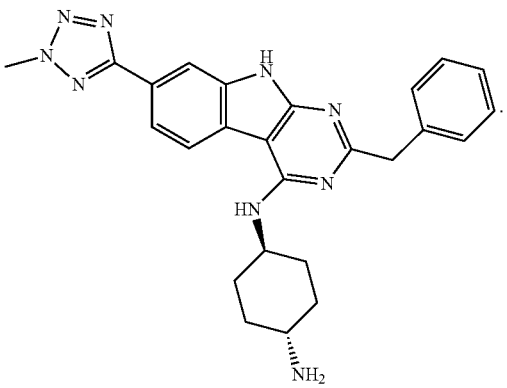 [SMILES: Cn1nnc(-c2ccc3c(c2)[nH]c2nc(Cc4ccccc4)nc(N[C@H]4CC[C@H](N)CC4)c23)n1]

In a supplemental embodiment, the compound of formula I is

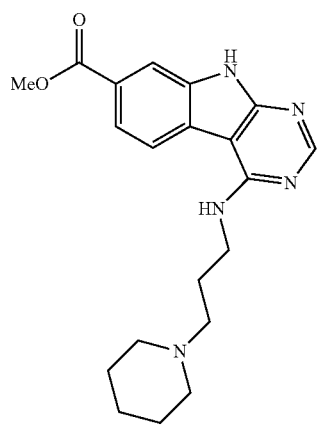 [SMILES: COC(=O)c1ccc2c(c1)[nH]c1ncnc(NCCCN3CCCCC3)c12]

or a pharmaceutically acceptable salt thereof.

In another embodiment, the compound of formula I is:

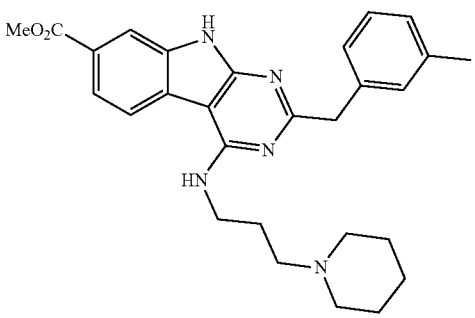 [SMILES: COC(=O)c1ccc2c(c1)[nH]c1nc(Cc3cccc(C)c3)nc(NCCCN3CCCCC3)c12]

1

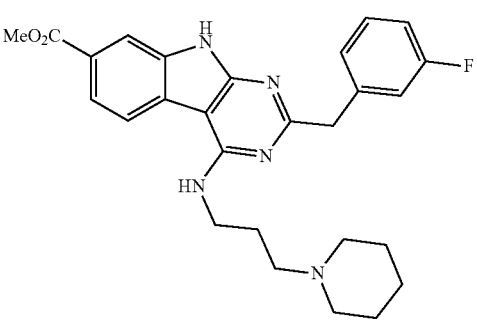 [SMILES: COC(=O)c1ccc2c(c1)[nH]c1nc(Cc3cccc(F)c3)nc(NCCCN3CCCCC3)c12]

2

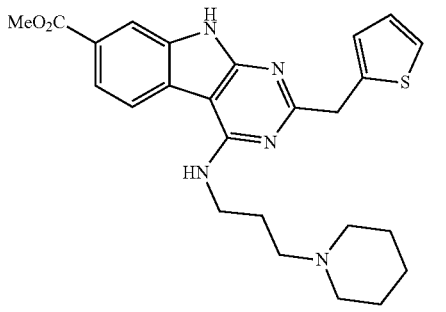

3

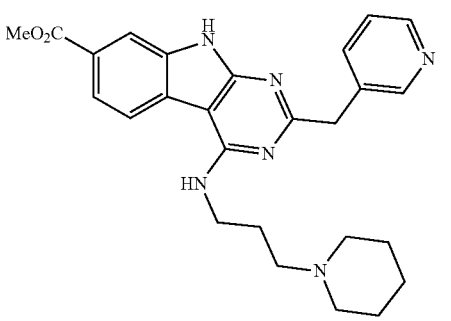 [SMILES: COC(=O)c1ccc2c(c1)[nH]c1nc(Cc3cccnc3)nc(NCCCN3CCCCC3)c12]

4

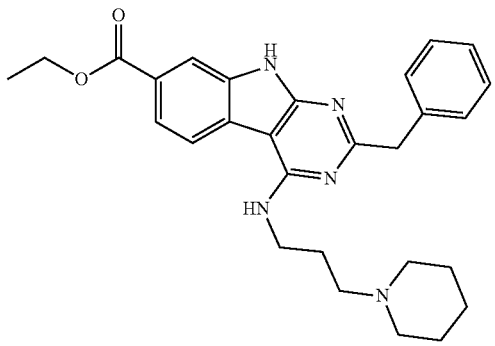 [SMILES: CCOC(=O)c1ccc2c(c1)[nH]c1nc(Cc3ccccc3)nc(NCCCN3CCCCC3)c12]

5

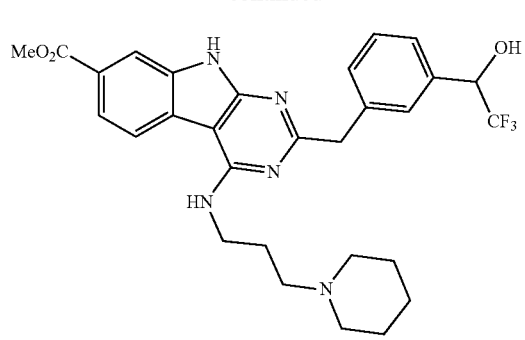 [SMILES: COC(=O)c1ccc2c(c1)[nH]c1nc(Cc3cccc(C(O)C(F)(F)F)c3)nc(NCCCN3CCCCC3)c12]
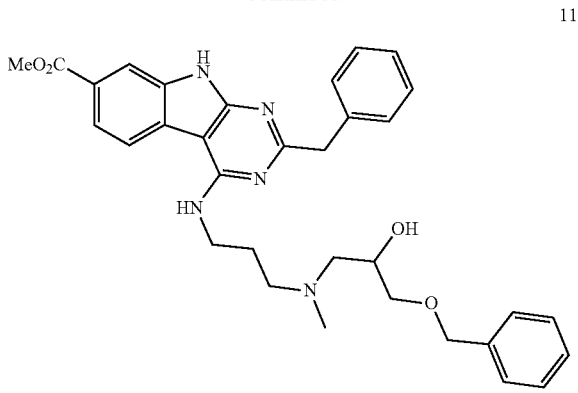
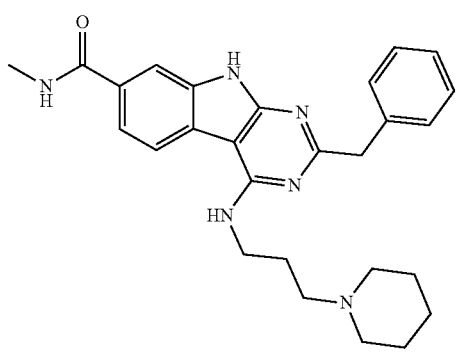
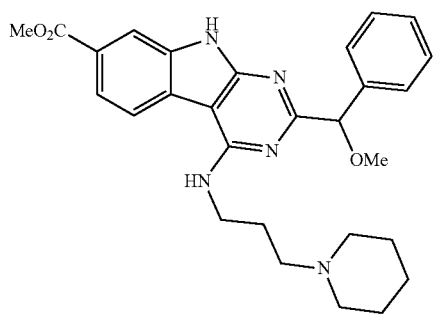
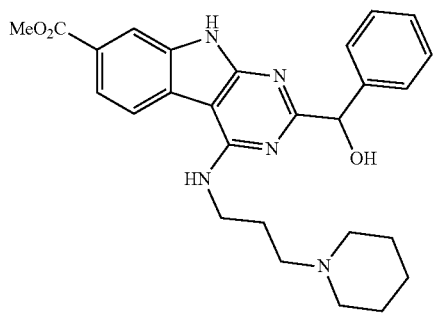

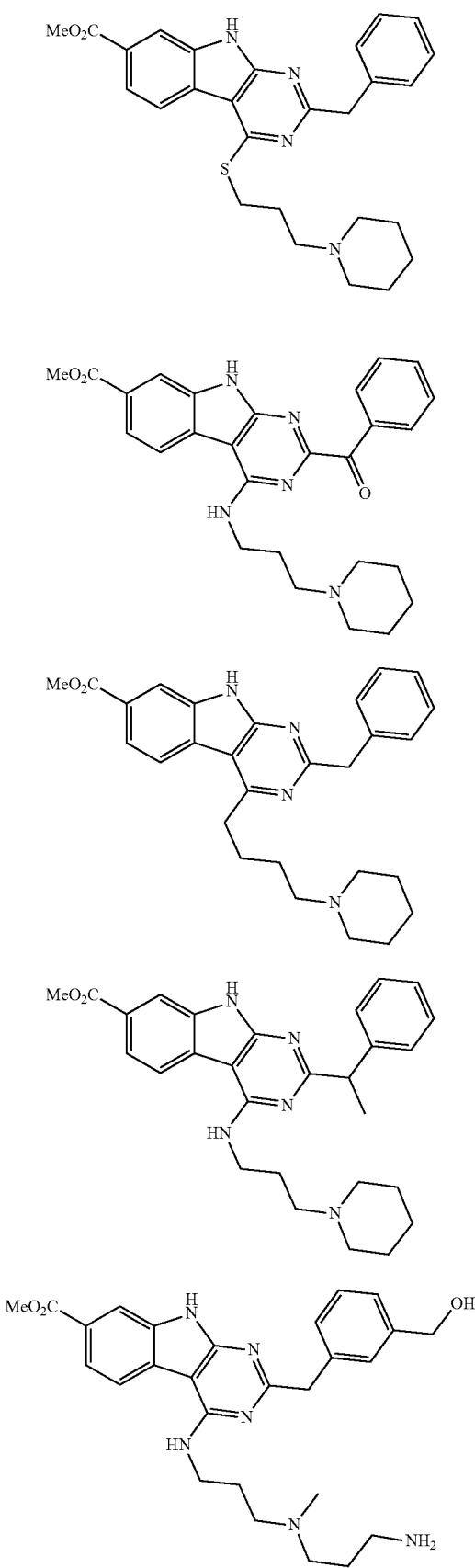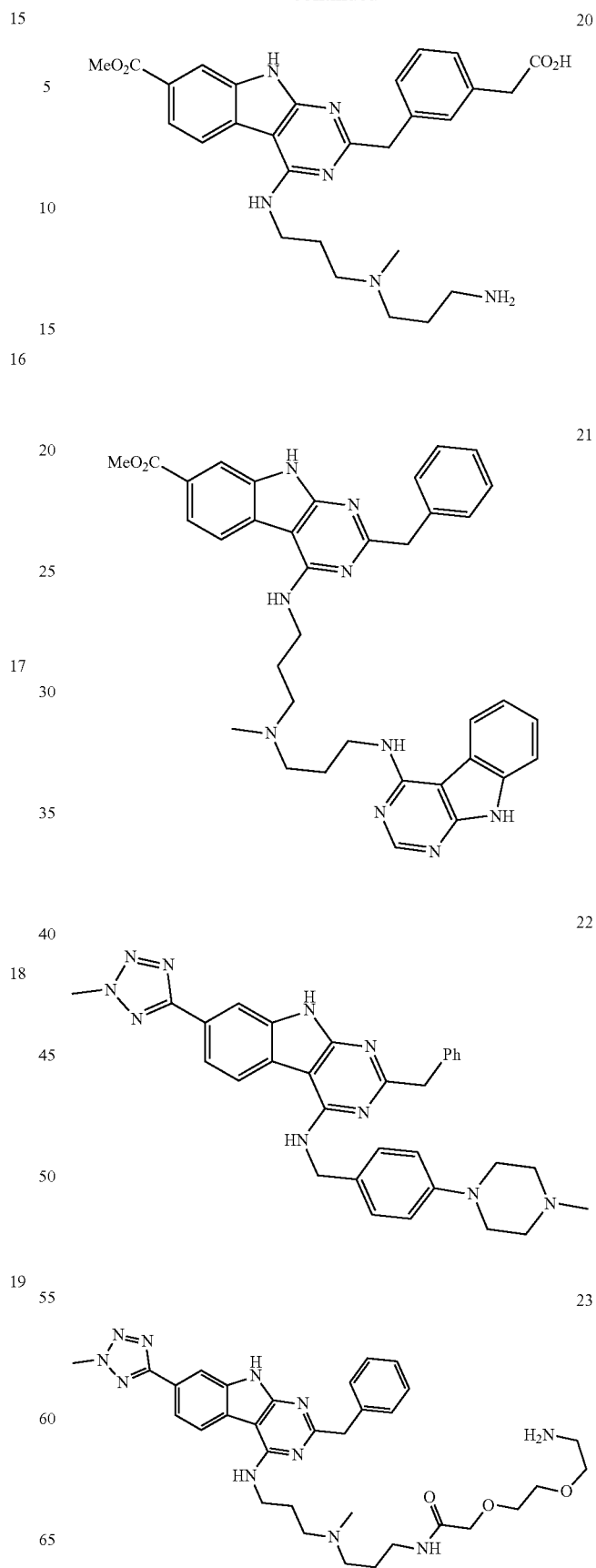

-continued
24
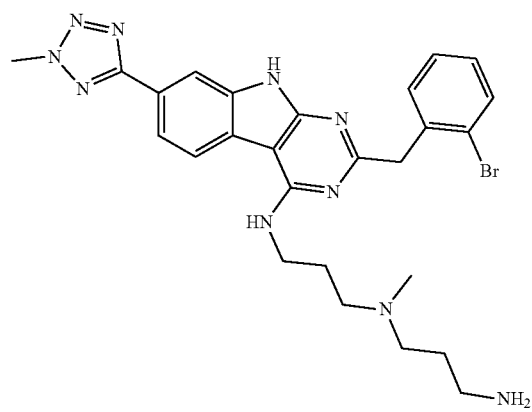
25
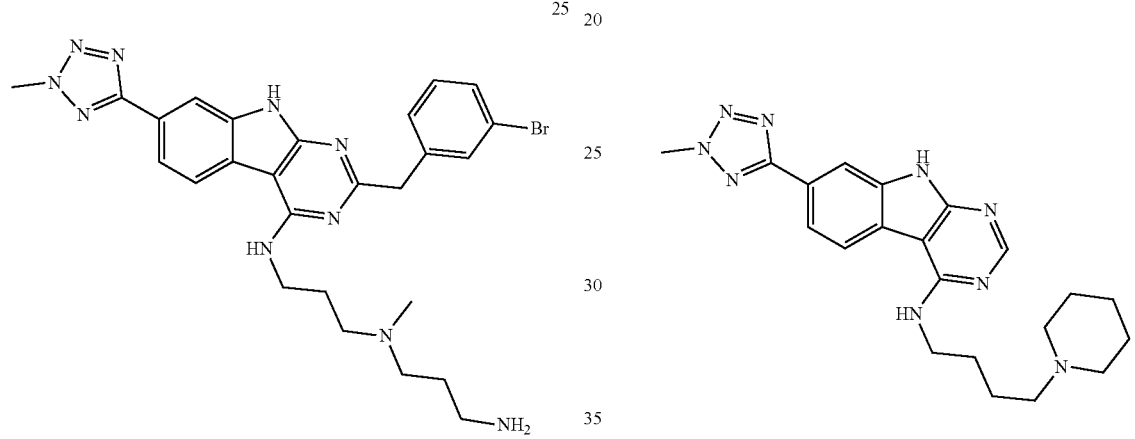
26
27
-continued
28
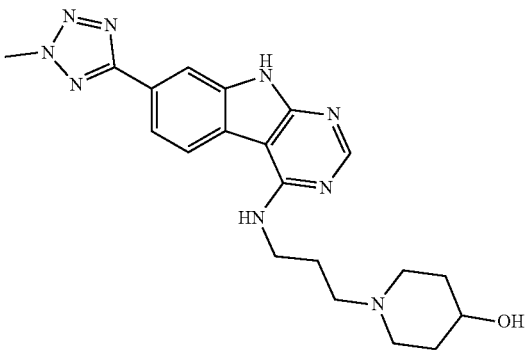
29
30
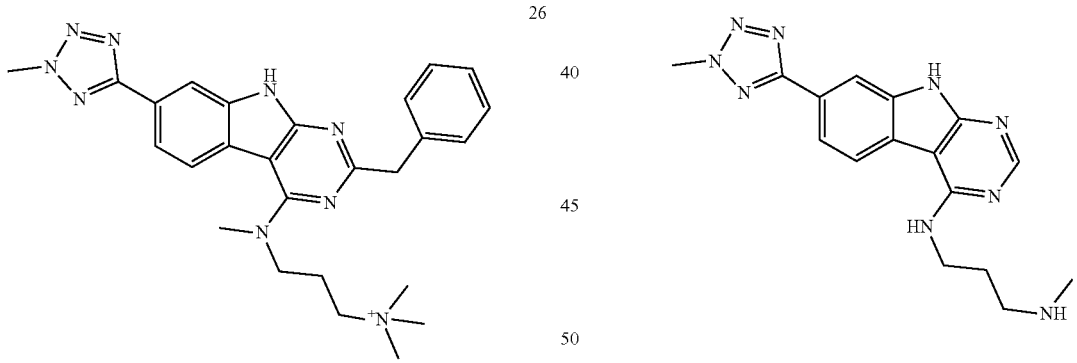
31
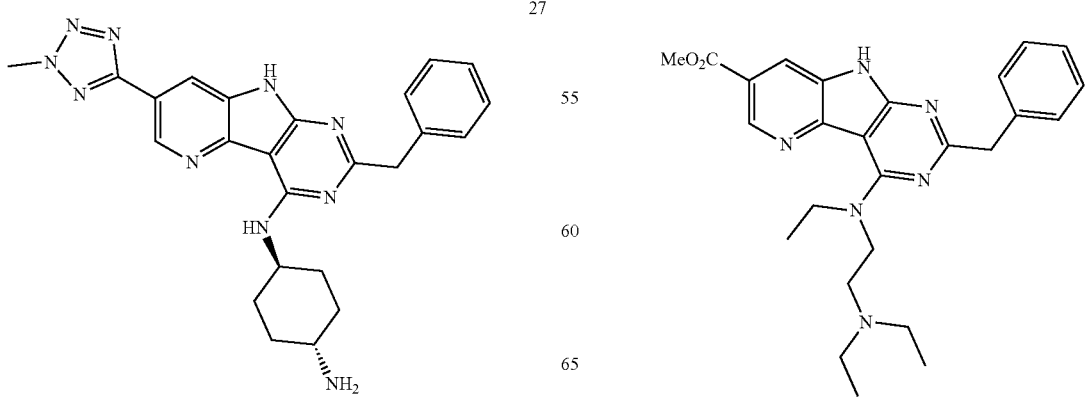

32
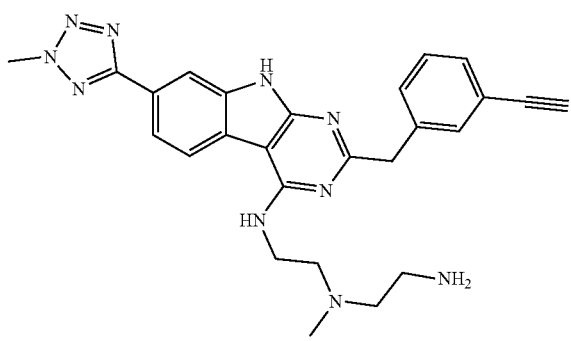
33
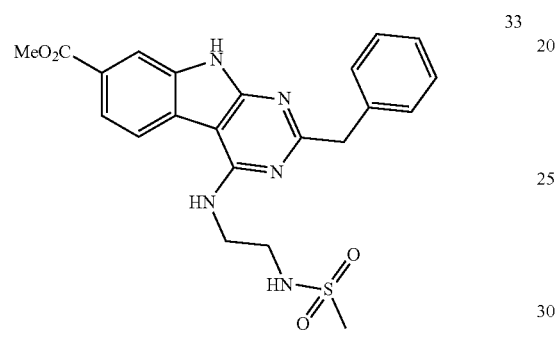
34
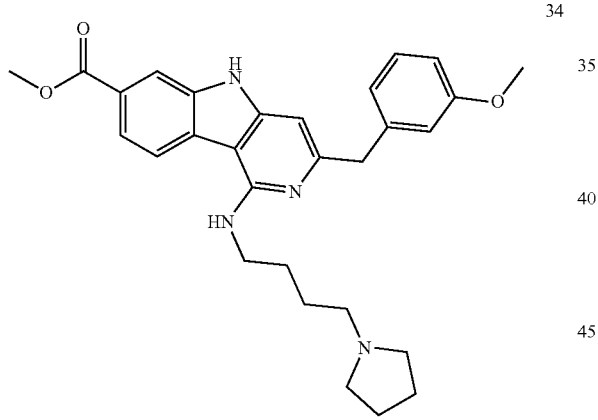
35
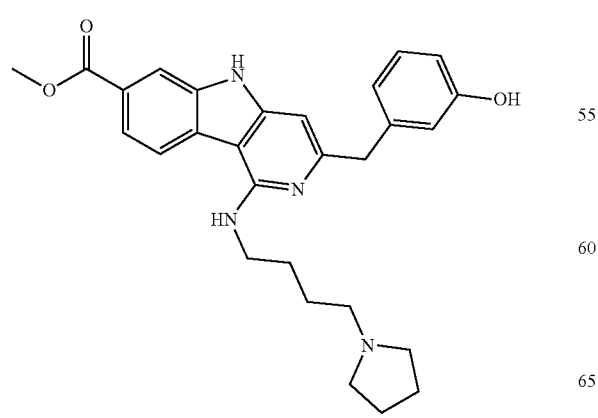
36
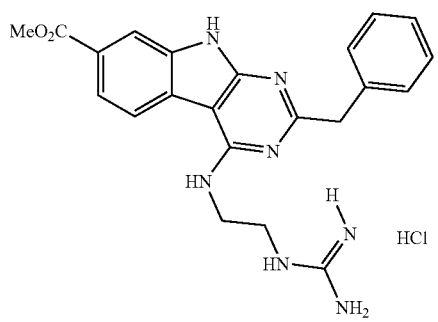
37
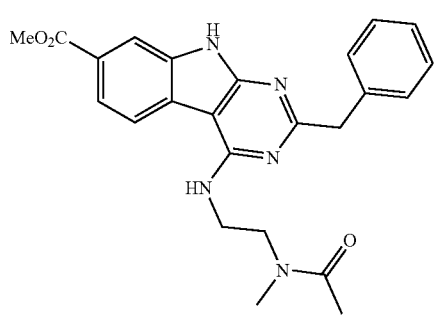
38
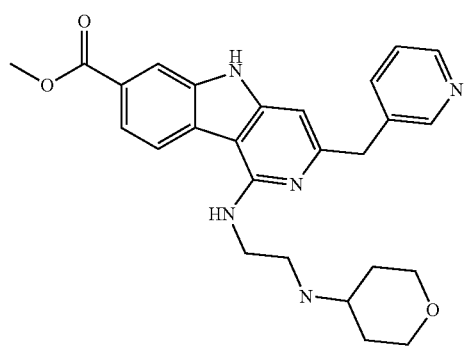
39
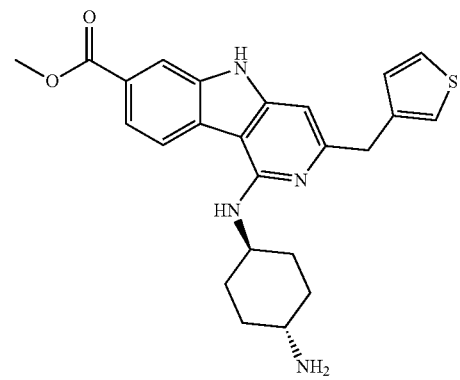

40
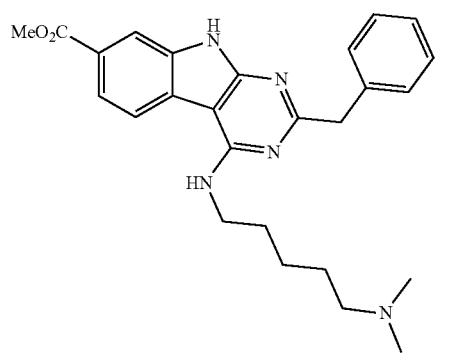
41
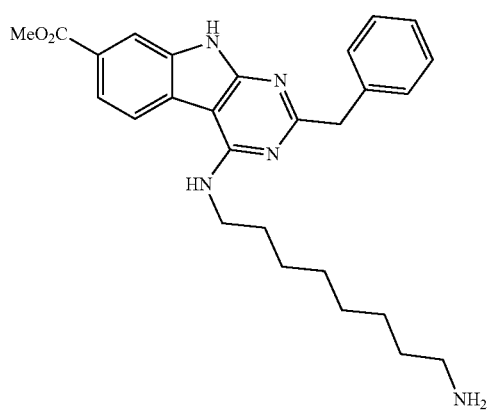
42
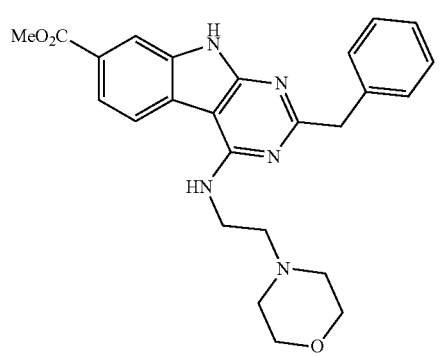
43
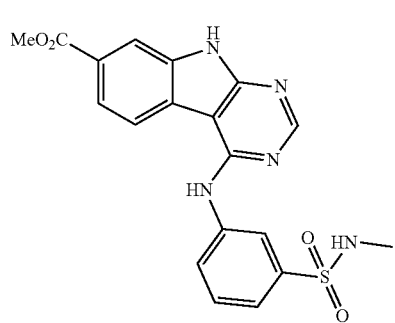
44
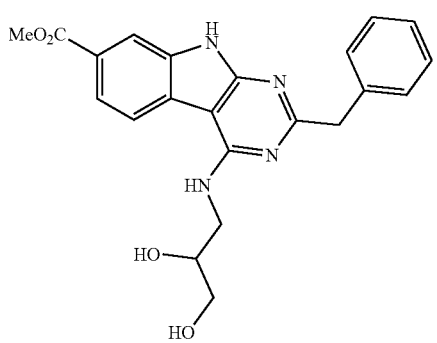
45
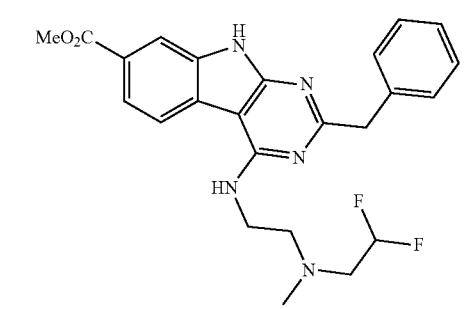
46
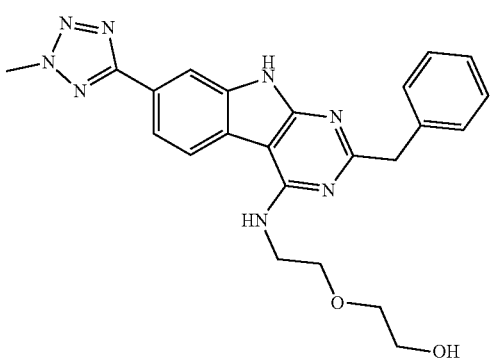
47
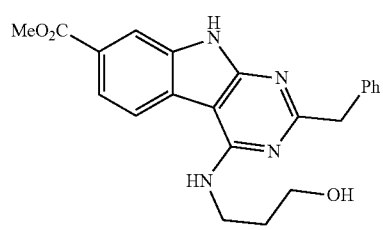
48
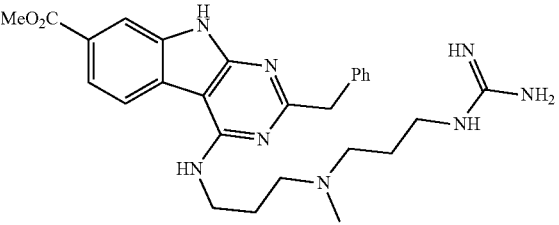

49
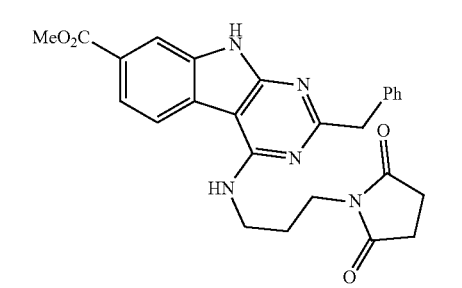
50
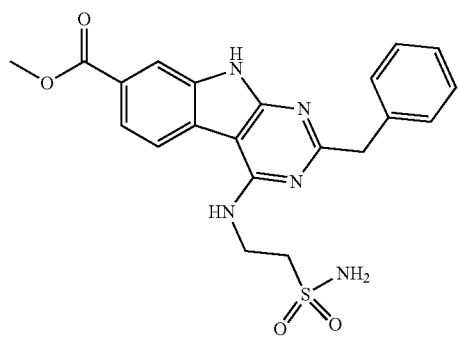
51
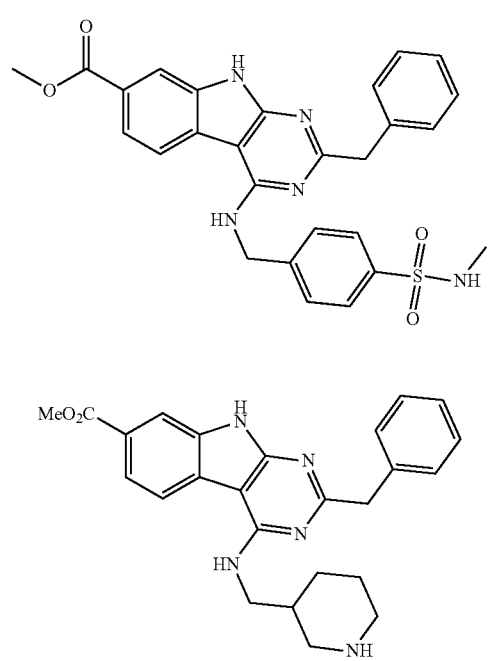
52
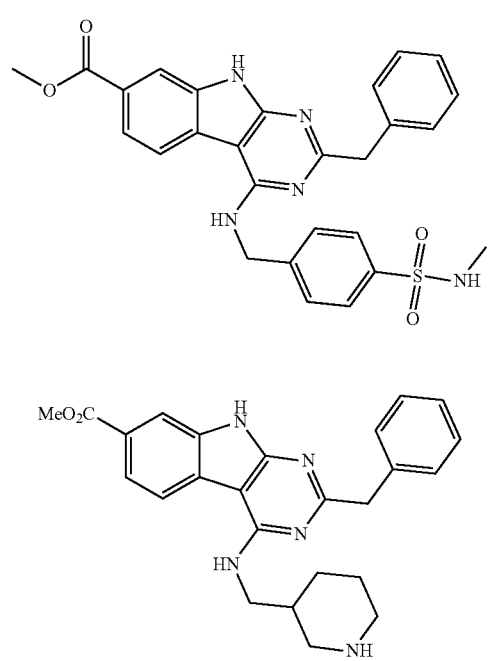
53
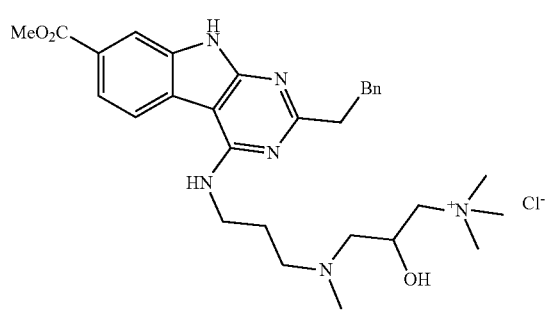
54
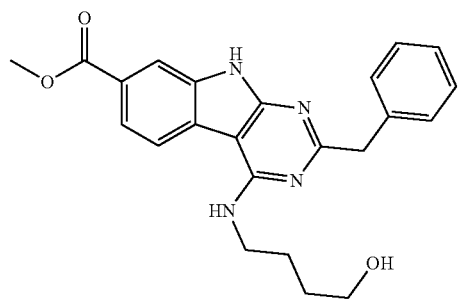
55
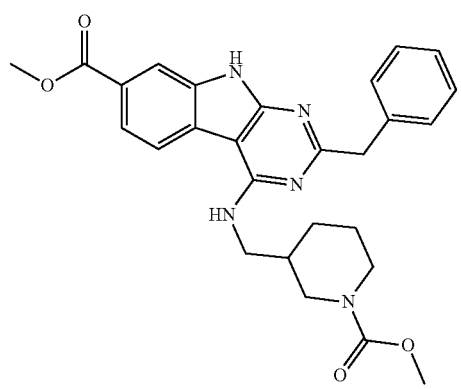
56
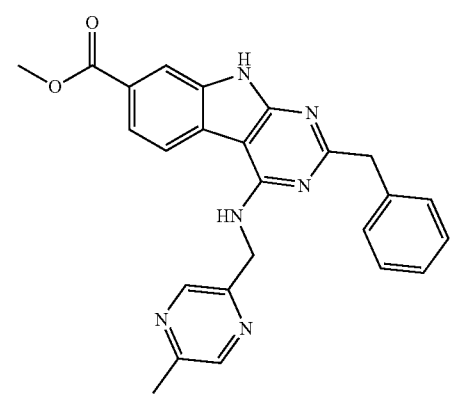
57
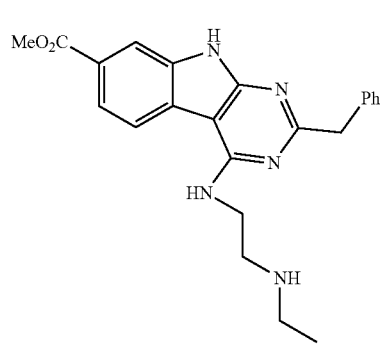

-continued

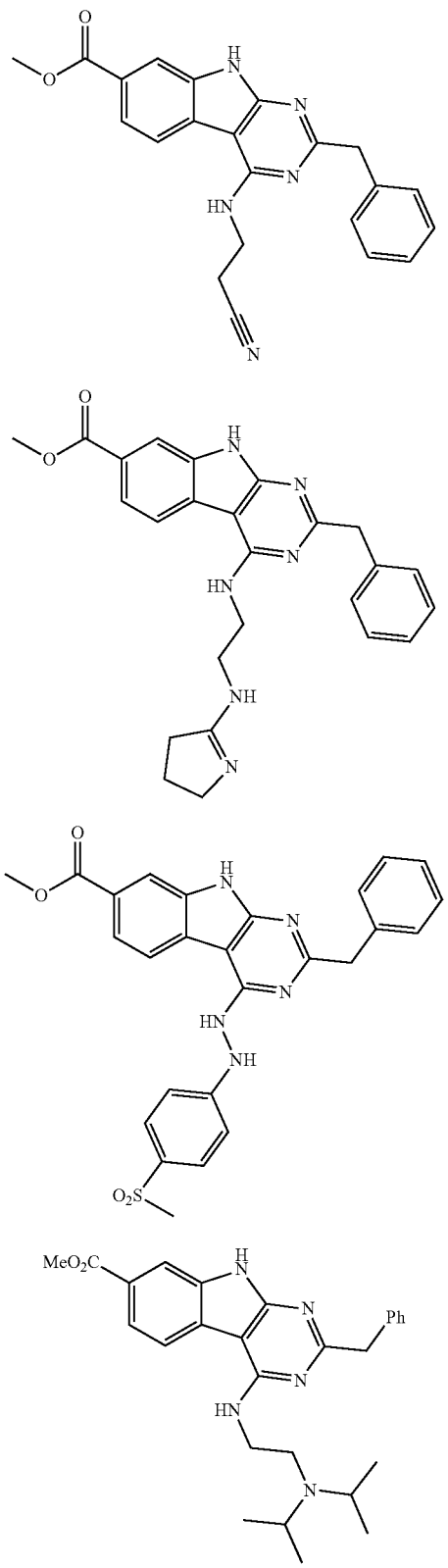

or a pharmaceutically acceptable salt thereof.

In another embodiment, the stem and/or progenitor cells are expanded in a bioreactor.

In an embodiment, the patient is a human or an animal.

In another embodiment, the animal is a mouse.

In a further embodiment, it is also encompass a method of treating a viral infection in the patient or the use of the graft of expanded stem and/or progenitor cells as described herein for treating a viral infection in the patient.

In an embodiment, the viral infection is a CMV infection, an EBV infection or an adenovirus cystitis.

In another embodiment, the DC cells and/or NK cells are expanded at 14 days, at 21 days, at 28 days, at 56 days, at 100 days, at 6 months, at 12 months or at 18 months in the patient.

In an embodiment, the inflammatory state is controlled in the patient.

In an embodiment, the graft comprises a dendritic cell population.

In another embodiment, the dendritic cell population are $CD86^+CD34^+$ cells.

In a further embodiment, the graft comprises 40-50% of dendritic cells.

In another embodiment, the graft comprises ⅓ of immature dendritic cells.

In an embodiment, the graft comprises mast cells.

In another embodiment, the graft comprises about 10% of mast cells.

In a preferred embodiment, the graft comprises $FCER1^+$ $CD34^+$ cells, $CD34^+CD45RA^+$ cells, $CD34^+CD86^+$ cells, $CD34^+CD45RA^-$ cells and $CD34^-$ cells.

BRIEF DESCRIPTION OF THE DRAWINGS

Reference will now be made to the accompanying drawings.

DETAILED DESCRIPTION

Figure 1:
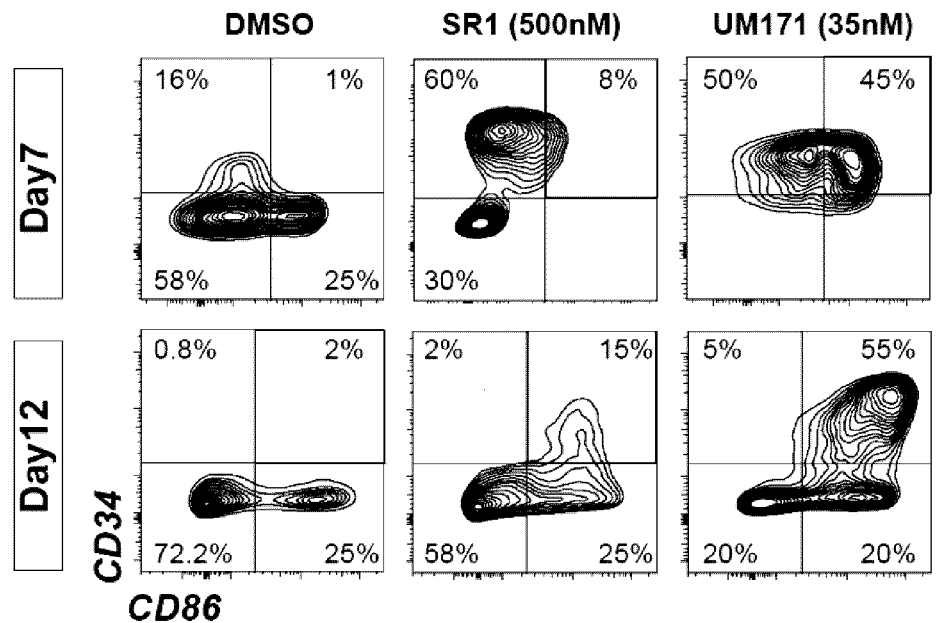
FIG. 1 illustrates that UM171 promotes the ex vivo expansion of primitive dendritic cell progenitors, wherein cord blood derived CD34+ cells were cultured for 7 and 14 days in HSC expansion media supplemented with vehicle (DMSO 0.1%), SR1 (500 nM) or UM171 (35 nM), frequency of dendritic cells precursors (iDC: CD34+CD86+) was evaluated by flow.

In accordance with the present disclosure, there is provided a method of expanding in vivo natural killer cells, dendritic cells, or a combination thereof after transplant with a cord blood graft expanded with UM171 or an analog thereof.

It is thus provided a method of expanding dendritic (DC) cells and/or natural killer (NK) cells in vivo in a patient comprising the steps of producing a graft of stem and progenitor cells cultured with UM171 or analogues therefrom and expanded before being administered to a patient. The expansion or increase in dendritic (DC) cells and natural killer (NK) cells population in the patient results in an increase immune response reducing transplant related mortality (TRM), severe graft-versus-host disease (GVHD), relapse, and/or severe viral infections.

Allogeneic hematopoietic stem cell (HSC) transplant is the best available therapy to cure patients with blood cancers. Cord blood (CB) is the most attractive source of stem cells.

It is known that a purine derivative, StemRegenin 1 (SR1), which promotes the ex vivo expansion of CD34+ cells, could expand HSCs but it was not possible not to reproduce expansion of long-term HSCs (Chen et al., 2012, Genes Dev., 26: 2499-2511). A major concern with SR1 is its ability to support leukemia stem cell growth in vitro (Pabst et al., 2014, Nature Methods, 11: 436-442).

Approximately 1% of CB cells express the CD34 surface antigen, which is made up of distinct subsets of stem and progenitor cells that have variable ability to provide short- or long-term hematopoiesis. These subsets contribute differently to early and long-term recovery of mature blood cell production. Only long-term HSCs can provide lifelong hematopoietic reconstitution. In vitro expansion of CB-derived short-term HSCs (progenitor cells) dramatically shortens time to neutrophil recovery post-transplant. However, most of the ex vivo cell expansion strategies described to date achieve this effect at the expense of long-term HSC loss, thereby compromising durable reconstitution with the risk of late graft failure. Accordingly, many of these strategies require the infusion of a $2^{nd}$ CB to ensure long-term engraftment. In sharp contrast, as described and encompassed herein, the molecule used in amplifying CB-derived short-term repopulating cells allow simultaneously expanding, not depleting, the long-term ones, paving the way for single expanded CB.

UM171 encompassed herein (see U.S. Pat. No. 9,409,906, the content of which is incorporated by reference), has an activity on primitive cells which is rapidly reversible if the compound is washed out from culture. UM171 does not independently trigger cell proliferation in the absence of growth factors; it is not mitogenic but rather prevents cell differentiation. UM171 was studied in a fed-batch culture system. Several negative cytokine regulators are released by mature cells as they are generated in CD34+CB cultures (Csaszar et al., 2012, Cell stem cell, 10: 218-229). The fed-batch encompassed herein leads to a reduction of endogenously produced negative regulators. This system requires much less media (<1 liter culture vs. 10 liters in most studies) and better supports the maintenance of CB-derived HSCs. A 7-day culture is optimal to maximize the quality of the cells. Importantly, the fed-batch culture is a closed system without the need for cell manipulation, minimizing contamination risk and facilitating the transition to cell product manufacturing.

As encompassed herein, the expansion of stem and/or progenitor cells can be conducted in a bioreactor consisting of any manufactured or engineered device or system that supports a biologically active environment such as cultured cells for expansion of said cells.

Accordingly, it is encompassed a method expanding in vivo natural killer cells, dendritic cells or a combination thereof after transplant with a cord blood graft using a compound of general formula I as defined herein:

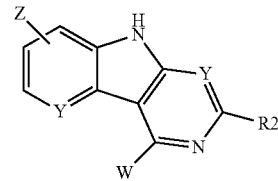

I or a salt or a prodrug thereof,
wherein:
each Y is independently selected from N and CH;
Z is —CN; —C(O)OR1; —C(O)N(R1)R3; —C(O)R1; or -heteroaryl optionally substituted with one or more RA or R4 substituents, wherein, when (R1) and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
W is —CN; —N(R1)R3; —C(O)OR1; —C(O)N(R1)R3; —NR1C(O)R1; —NR1C(O)OR1; —OC(O)N(R1)R3; —OC(O)R1; —C(O)R1; —NR1C(O)N(R1)R3; —NR1S(O)$_2$R1; -benzyl optionally substituted with 1, 2 or 3 RA or R1 substituents; —X-L-(X-L)$_n$; —N(R1)R3; —X-L-(X-L)$_n$-heteroaryl optionally substituted with one or more RA or R4 substituents attached on either or both the L and heteroaryl groups; —X-L-(X-L)$_n$-heterocyclyl optionally substituted with one or more RA or R4 substituents attached on either or both the L and heterocyclyl groups; —X-L-(X-L)$_n$-aryl optionally substituted with one or more RA or R4 substituents; —X-L-(X-L)$_n$-NR1RA or —(N(R1)-L)$_n$-N*R1 R3R5 R6$^-$, wherein n is an integer equal to either 0, 1, 2, 3, 4, or 5,
and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently selected from C, O, S, and NR1;
L is each independently —C$_{1-6}$ alkylene; —C$_{2-6}$ alkenylene; —C$_{2-6}$ alkynylene; —C$_{3-7}$ cycloalkylene, which optionally includes one or more other heteroatom selected from N, O and S; or —C$_{3-7}$ cycloalkenylene, which optionally includes one or more other heteroatom selected from N, O and S, wherein the alkylene, the alkenylene, the alkynylene, the cycloalkylene and the cycloalkenylene groups are each independently optionally substituted with one or two R4 or RA substituent;

R1 is each independently —H; —$C_{1-6}$ alkyl; —$C_{2-6}$ alkenyl; —$C_{2-6}$ alkynyl; —$C_{3-7}$ cycloalkyl; —$C_{3-7}$ cycloalkenyl; —$C_{1-5}$ perfluorinated; -heterocyclyl; -aryl; -heteroaryl; or -benzyl, wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is —H; —$C_{1-6}$ alkyl, optionally substituted with one more RA substituents; —C(O)R4; -L-heteroaryl optionally substituted with one or more RA or R4 substituents; -L-heterocyclyl optionally substituted with one or more RA or R4; or -L-aryl optionally substituted with one or more RA or R4 substituents;

R3 is each independently —H; —$C_{1-6}$ alkyl; —$C_{2-6}$ alkenyl; —$C_{2-6}$ alkynyl; —$C_{3-7}$ cycloalkyl; —$C_{3-7}$ cycloalkenyl; —$C_{1-5}$ perfluorinated; -heterocyclyl; -aryl; -heteroaryl; or -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R4 is each independently —H; —$C_{1-6}$ alkyl; —$C_{2-6}$ alkenyl; —$C_{2-6}$ alkynyl; —$C_{3-7}$ cycloalkyl; —$C_{3-7}$ cycloalkenyl; —$C_{1-5}$ perfluorinated; -heterocyclyl; -aryl; -heteroaryl, or -benzyl; wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently —$C_{1-6}$ alkyl; —$C_{1-6}$ alkylene-$C_{2-6}$ alkenyl which optionally includes one or more other heteroatom selected from N, O and S; —$C_{1-6}$ alkylene-$C_{2-6}$ alkynyl which optionally includes one or more other heteroatom selected from N, O and S; -L-aryl which optionally includes one or more RA or R4 substituents; -L-heteroaryl which optionally includes one or more RA or R4 substituents; —$C_1$_alkylene-C(O)O—; —$C_{1-6}$ alkylene-C(O)OR1; —$C_{1-6}$ alkylene-CN; —$C_{1-6}$ alkylene-C(O)NR1R3, wherein R1 and R3 optionally they join together with the nitrogen atom to form a 3 to 7-membered ring which optionally includes one or more other heteroatom selected from N, O and S; or —$C_{1-6}$ alkylene-OH;

R6 is halogen; —OC(O)$CF_3$; or —OC(O)R1;

RA is each independently -halogen; —$CF_3$; —OR1; -L-OR1; —O$CF_3$; —SR1; —CN; —$NO_2$; —NR1R3; -L-NR1R1; —C(O)OR1; —S(O)$_2$R4; —C(O)N(R1)R3; —NR1C(O)R1; —NR1C(O)OR1; —OC(O)N(R1)R3; —OC(O)R1; —C(O)R4; —NHC(O)N(R1)R3; —NR1C(O)N(R1)R3; or —$N_3$; and Rd is each independently —H; —$C_{1-6}$ alkyl; —$C_{2-6}$ alkenyl; —$C_{2-6}$ alkynyl; —$C_{3-7}$ cycloalkyl; —$C_{3-7}$ cycloalkenyl; —$C_{1-5}$ perfluorinated; -benzyl; or -heterocyclyl.

In one embodiment, Z is —C(O)OR1, or -heteroaryl optionally substituted with one or more RA or R1 substituents, R2 is H, —$C_{1-6}$ alkyl optionally substituted with one or more RA substituents or -L-aryl optionally substituted with one or more RA or R4 substituents, W is —N(R1)R3 wherein R1 is $C_{3-7}$ cycloalkyl substituted by RA and R3 is H.

In one embodiment, Z is —C(O)O—$C_{1-4}$ alkyl or 5-membered ring heteroaryl, the heteroaryl comprising 2-4 heteroatoms (N or O), R2 is H, or -L-aryl optionally substituted by halogen, OR1, $C_{1-6}$ alkyl optionally substituted by RA, C(O)R4, -heterocyclyl, C(O)OR4 OR $C_{2-6}$ alkynyl, W is —N(R1)R3 wherein R1 is cyclohexyl substituted by RA, and R3 is H.

In one embodiment, Z is COOMe, COOEt, tetrazole or oxadiazole.

In one embodiment, R2 is =H, or —CH2-aryl optionally substituted by substituted by halogen, OR1, $C_{1-6}$ alkyl optionally substituted by RA, C(O)R4, -heterocyclyl, C(O)OR4 OR $C_{2-6}$ alkynyl, wherein the aryl is phenyl.

In one embodiment, R2 is H, —$C_{1-6}$ alkylene-heteroaryl or —$C_{1-6}$ alkylene-aryl, optionally substituted with one or more RA or R4 substituents.

In accordance with another embodiment, the compound is of Formula I, IA or IIA wherein Z is $CO_2$Me or 2-methyl-2H-tetrazol-5-yl;

R2 is benzyl, or H; and

W is NH-L-N(R1)R3 wherein L is $C_{2-4}$ alkylene or $C_{3-7}$ cycloalkylene and R1 and R3 is $C_{1-4}$ alkyl or H; or R1 and R3 join together with the nitrogen atom to which they are attached to form a 3 to 7-membered ring, which optionally includes one or more other heteroatom selected from N, O and S, optionally the ring is substituted with one or more RA or R4.

In accordance with another embodiment, the compound is of Formula I wherein W is

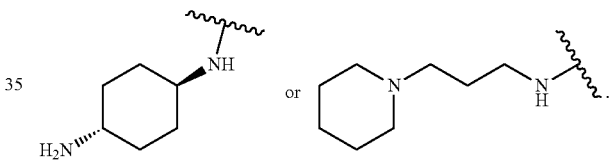

The compounds of formula I (including the representative compounds set forth below) disclosed herein, including the preparation and characterization thereof, are described in PCT publication No. WO 2013/110198, the content of which is incorporated by reference in its entirety as well as in the synthetic methodology section found below.

As used herein, the term "alkyl" is intended to include both branched and straight chain saturated aliphatic hydrocarbon groups having the specified number of carbon atoms, for example, C1-C6 in C1-C6 alkyl is defined as including groups having 1, 2, 3, 4, 5 or 6 carbons in a linear or branched saturated arrangement. Examples of C1-C6 alkyl as defined above include, but are not limited to, methyl, ethyl, n-propyl, i-propyl, n-butyl, t-butyl, i-butyl, pentyl, and hexyl.

As used herein, the term "cycloalkyl" is intended to mean a monocyclic saturated aliphatic hydrocarbon group having the specified number of carbon atoms therein, for example, C3-C7 in C3-C7 cycloalkyl is defined as including groups having 3, 4, 5, 6 or 7 carbons in a monocyclic saturated arrangement. Examples of C3-C7 cycloalkyl as defined above include, but are not limited to, cyclopropyl, cyclobutyl, cyclopentyl, cyclohexyl and cycloheptyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, C2-C6 in C2-C6 alkenyl is defined as including groups having 2, 3, 4, 5 or 6 carbons in a linear or branched arrangement, at least two of the carbon atoms being bonded together by a double bond. Examples of C2-C6 alkenyl include, but are not limited to, ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example C2-C4 alkynyl is defined as including groups having 2, 3 or 4 carbon atoms in a chain, at least two of the carbon atoms being bonded together by a triple bond. Examples of such alkynyl include, but are not limited to, ethynyl, 1-propynyl, 2-propynyl and the like.

As used herein, the term "cycloalkenyl" is intended to mean a monocyclic saturated aliphatic hydrocarbon group having the specified number of carbon atoms therein, for example, C3-C7 in C3-C7 cycloalkenyl is defined as including groups having 3, 4, 5, 6 or 7 carbons in a monocyclic arrangement. Examples of C3-C7 cycloalkenyl as defined above include, but are not limited to, cyclopentenyl, cyclohexenyl and the like.

As used herein, the term "halo" or "halogen" is intended to mean fluorine, chlorine, bromine or iodine.

As used herein, the term "haloalkyl" is intended to mean an alkyl as defined above, in which each hydrogen atom may be successively replaced by a halogen atom. Examples of haloalkyl include, but are not limited to, $CH_2F$, $CHF_2$ and $CF_3$.

As used herein, the term "aryl," either alone or in combination with another radical, means a carbocyclic aromatic monocyclic group containing 6 carbon atoms which may be further fused to a second 5- or 6-membered carbocyclic group which may be aromatic, saturated or unsaturated. Examples of aryl include, but are not limited to, phenyl, indanyl, 1-naphthyl, 2-naphthyl, tetrahydronaphthyl and the like. The aryl may be connected to another group either at a suitable position on the cycloalkyl ring or the aromatic ring.

As used herein, the term "heteroaryl" is intended to mean a monocyclic or bicyclic ring system of up to 10 atoms, wherein at least one ring is aromatic, and contains from 1 to 4 hetero atoms selected from the group consisting of O, N, and S. The heteroaryl may be attached either via a ring carbon atom or one of the heteroatoms. Examples of heteroaryl include, but are not limited to, thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, tetrazolyl, oxadiazolyl, thiadiazolyl, thienyl, pyrimido-indolyl, pyrido-indolyl, pyrido-pyrrolo-pyrimidinyl, pyrrolo-dipyridinyl and fluoroscein derivatives.

As used herein, the term "heterocycle," "heterocyclic" or "heterocyclyl" is intended to mean a 3, 4, 5, 6, or 7 membered non-aromatic ring system containing from 1 to 4 heteroatoms selected from the group consisting of O, N and S. Examples of heterocycles include, but are not limited to, pyrrolidinyl, tetrahydrofuranyl, piperidyl, 3,5-dimethylpiperidyl, pyrrolinyl, piperazinyl, imidazolidinyl, morpholinyl, imidazolinyl, pyrazolidinyl, pyrazolinyl, tetrahydro-1H-thieno[3,4-d]imidazole-2(3H)-one, diazirinyl, and the like, where the attachment to the ring can be on either the nitrogen atom or a carbon atom of the ring such as described hereafter:

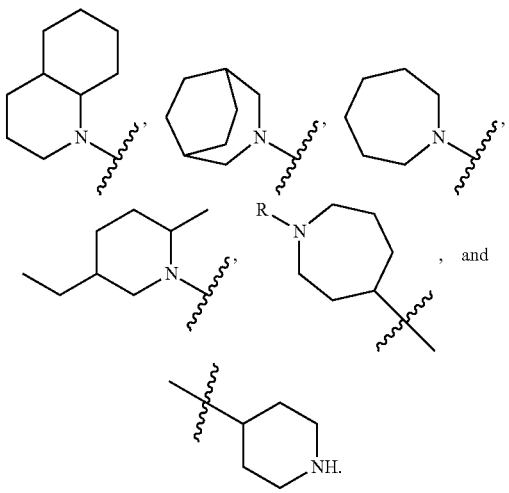

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

As used herein, the term "subject" or "patient" is intended to mean humans and non-human mammals such as primates, cats, dogs, swine, cattle, sheep, goats, horses, rabbits, rats, mice and the like.

If the substituents themselves are incompatible with the synthetic methods described herein, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, "Protecting Groups in Chemical Synthesis" (4th ed.), John Wiley & Sons, NY (2007), which is incorporated herein by reference in its entirety. Examples of protecting groups used throughout include, but are not limited to, Fmoc, Bn, Boc, CBz and $COCF_3$. In some instances, a substituent may be specifically selected to be reactive under the reaction conditions used in the methods described herein. Under these circumstances, the reaction conditions convert the selected substituent into another substituent that is either useful in an intermediate compound in the methods described herein or is a desired substituent in a target compound.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compounds encompassed herein or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds encompassed herein may exist as a mix of epimers. Epimers means diastereoisomers that have the opposite configuration at only one of two or more stereogenic centers present in the respective compound.

Compounds encompassed herein may exist in Zwitterionic form and the present includes Zwitterionic forms of these compounds and mixtures thereof.

In addition, the compounds encompassed herein also may exist in hydrated and anhydrous forms. Hydrates of the compound of any of the formulas described herein are included. In a further embodiment, the compound according to any of the formulas described herein is a monohydrate. In embodiments, the compounds described herein comprise about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In other embodiments, the compounds described herein comprise, about 0.1% or more, about 0.5% or more, about 1% or more, about 2% or more, about 3% or more, about 4% or more, about 5% or more, or about 6% or more by weight of water.

It may be convenient or desirable to prepare, purify, and/or handle the compound in the form of a prodrug. Thus, the term "prodrug", as used herein, pertains to a compound which, when metabolized (e.g., in vivo), yields the desired active compound. Typically, the prodrug is inactive, or less active than the desired active compound, but may provide advantageous handling, administration, or metabolic properties. Unless otherwise specified, a reference to a particular compound also includes prodrugs thereof.

In an embodiment, a compound of formula I, more specifically UM171 or derivatives can be used alone or in combination with a AHR for the differentiation of monocytic derived AML cell lines into immature and mature functional DCs.

UM171 as the following structure:

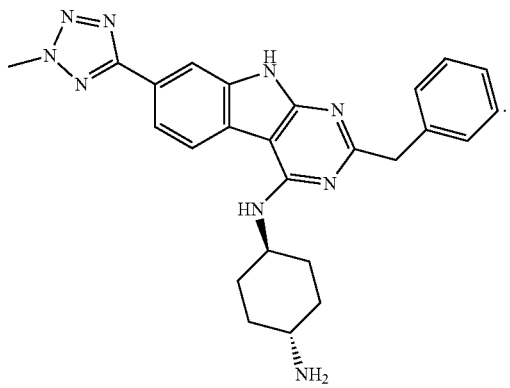

Accordingly, also encompassed are the following compounds:

| | Structure | *EC$_{50}$ |
|---|---|---|
| 1 | (MeO$_2$C-substituted pyrimido-indole with 3-methylbenzyl and 3-(piperidin-1-yl)propylamino substituents) | 38 |
| 2 | (MeO$_2$C-substituted pyrimido-indole with 3-fluorobenzyl and 3-(piperidin-1-yl)propylamino substituents) | 20 |
| 3 | (MeO$_2$C-substituted pyrimido-indole with thiophen-2-ylmethyl and 3-(piperidin-1-yl)propylamino substituents) | 8.0 |
| 4 | (MeO$_2$C-substituted pyrimido-indole with pyridin-3-ylmethyl and 3-(piperidin-1-yl)propylamino substituents) | 14 |

-continued

| | Structure | *EC$_{50}$ |
|---|---|---|
| 5 | (ethyl ester-substituted pyrimido-indole with benzyl and 3-piperidin-1-yl-propylamino substituents) | 154 |
| 6 | (MeO$_2$C-substituted pyrimido-indole with 3-(1-hydroxy-2,2,2-trifluoroethyl)benzyl and 3-piperidin-1-yl-propylamino substituents) | 16 |
| 7 | (MeO$_2$C-substituted pyrimido-indole with 3-(trifluoroacetyl)benzyl and 3-piperidin-1-yl-propylamino substituents) | 31 |
| 8 | (MeO$_2$C-substituted pyrimido-indole with naphthalen-2-ylmethyl and 3-piperidin-1-yl-propylamino substituents) | 150 |

-continued

| | Structure | *EC₅₀ |
|---|---|---|
| 9 | 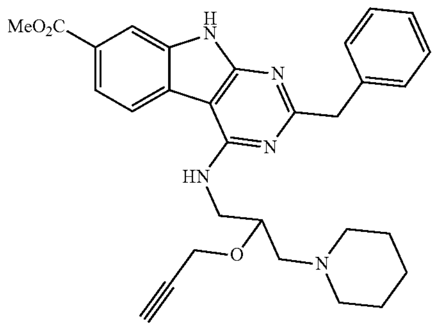 [SMILES: C#CCOC(CNc1nc(Cc2ccccc2)nc2[nH]c3cc(C(=O)OC)ccc3c12)CN1CCCCC1] | 24 |
| 10 | 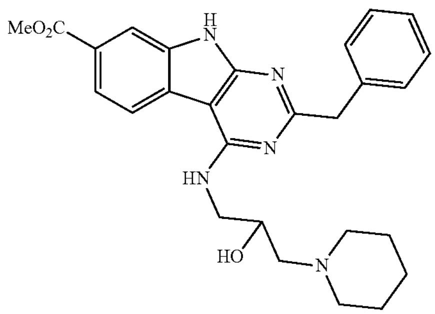 [SMILES: COC(=O)c1ccc2c(c1)[nH]c1nc(Cc3ccccc3)nc(NCC(O)CN3CCCCC3)c12] | 7.0 |
| 11 | 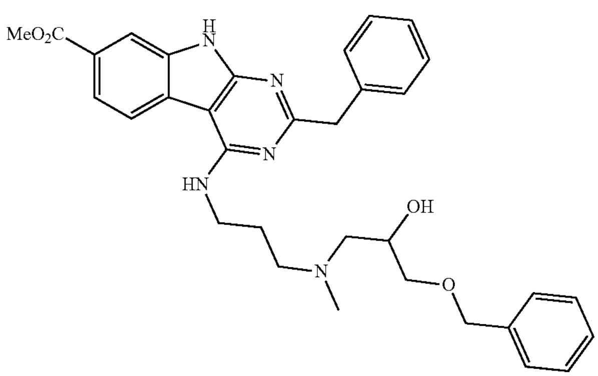 [SMILES: COC(=O)c1ccc2c(c1)[nH]c1nc(Cc3ccccc3)nc(NCCCN(C)CC(O)COCc3ccccc3)c12] | 101 |
| 12 | 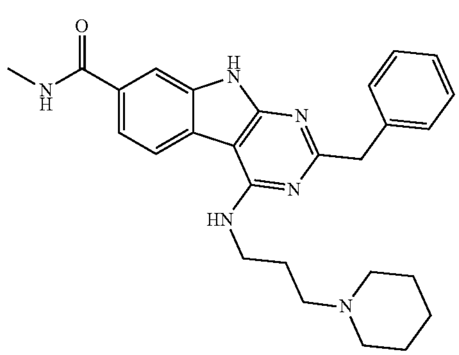 [SMILES: CNC(=O)c1ccc2c(c1)[nH]c1nc(Cc3ccccc3)nc(NCCCN3CCCCC3)c12] | 2445 |

-continued

| | Structure | *EC$_{50}$ |
|---|---|---|
| 13 | 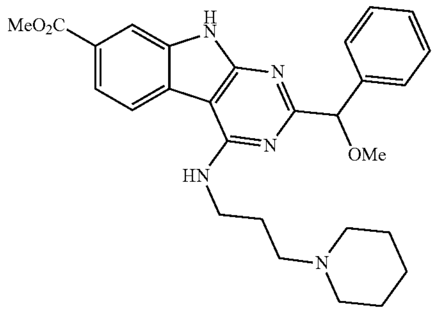 [SMILES: COC(=O)c1ccc2c(c1)[nH]c1nc(C(OC)c3ccccc3)nc(NCCCN3CCCCC3)c12] | 68 |
| 14 | 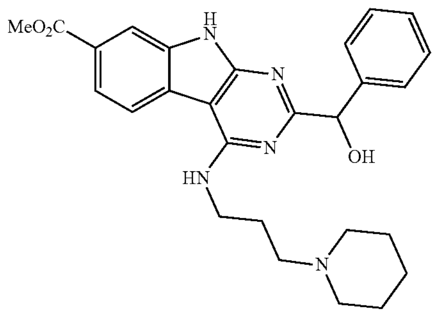 [SMILES: COC(=O)c1ccc2c(c1)[nH]c1nc(C(O)c3ccccc3)nc(NCCCN3CCCCC3)c12] | 4.0 |
| 15 | 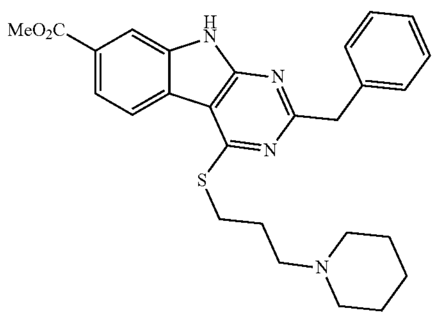 [SMILES: COC(=O)c1ccc2c(c1)[nH]c1nc(Cc3ccccc3)nc(SCCCN3CCCCC3)c12] | 327 |
| 16 | 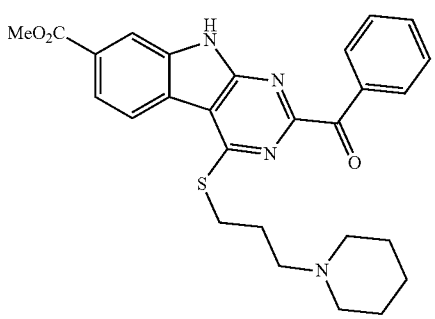 [SMILES: COC(=O)c1ccc2c(c1)[nH]c1nc(C(=O)c3ccccc3)nc(SCCCN3CCCCC3)c12] | 5.0 |
| 17 | 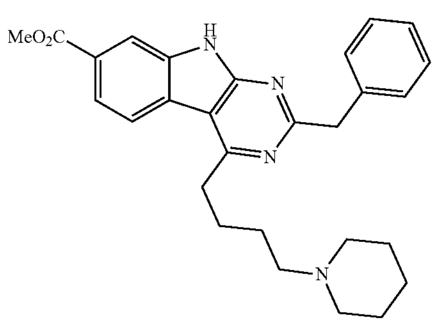 [SMILES: COC(=O)c1ccc2c(c1)[nH]c1nc(Cc3ccccc3)nc(CCCCN3CCCCC3)c12] | 15 |

-continued
| | Structure | *EC$_{50}$ |
|---|---|---|
| 18 | 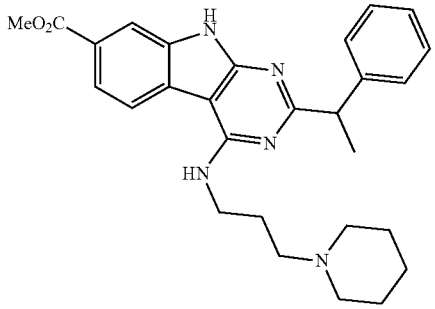 [SMILES: COC(=O)c1ccc2c(c1)[nH]c1nc(C(C)c3ccccc3)nc(NCCCN3CCCCC3)c12] | 67 |
| 19 | 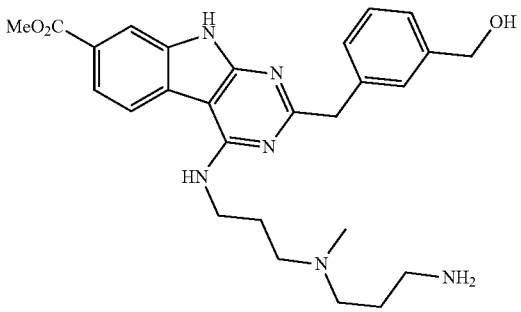 [SMILES: COC(=O)c1ccc2c(c1)[nH]c1nc(Cc3cccc(CO)c3)nc(NCCCN(C)CCCN)c12] | 38 |
| 20 | 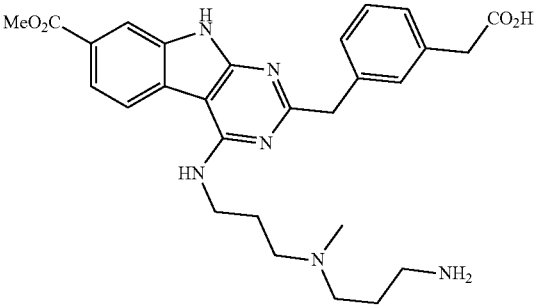 [SMILES: COC(=O)c1ccc2c(c1)[nH]c1nc(Cc3cccc(CC(=O)O)c3)nc(NCCCN(C)CCCN)c12] | 113 |
| 21 | 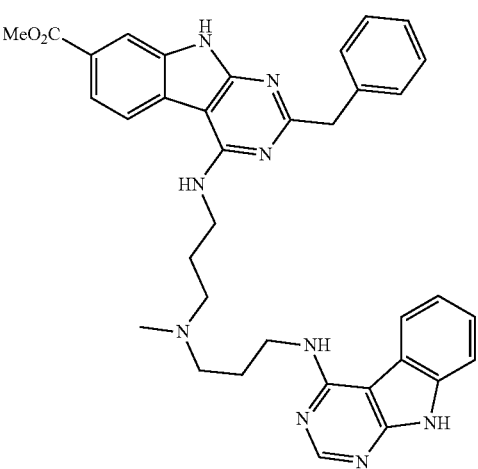 [SMILES: COC(=O)c1ccc2c(c1)[nH]c1nc(Cc3ccccc3)nc(NCCCN(C)CCCNc3ncnc4[nH]c5ccccc5c34)c12] | 19 |

-continued
| | Structure | *EC$_{50}$ |
|---|---|---|
| 22 | 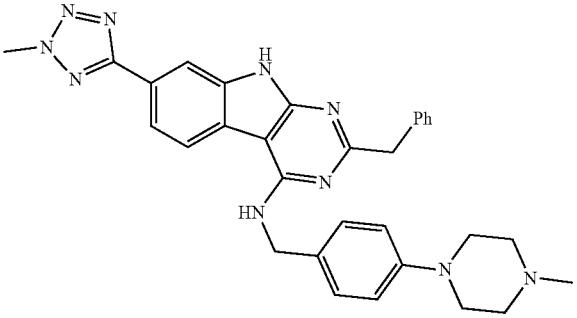 | 100 |
| 23 | 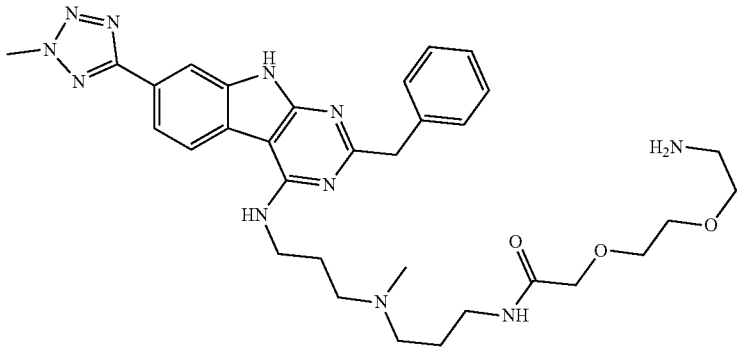 [SMILES: CN(CCCNC(=O)COCCOCCN)CCCNc1nc(Cc2ccccc2)nc2[nH]c3cc(-c4nnn(C)n4)ccc3c12] | 249 |
| 24 | 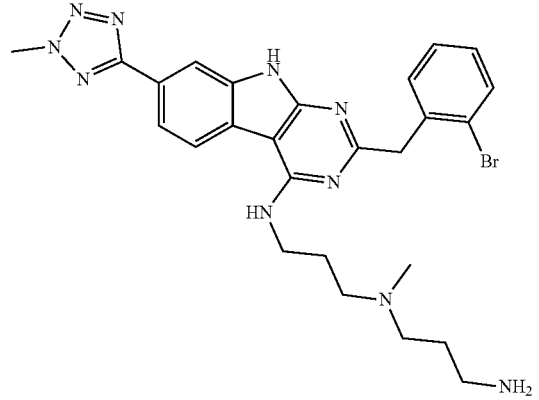 [SMILES: CN(CCCN)CCCNc1nc(Cc2ccccc2Br)nc2[nH]c3cc(-c4nnn(C)n4)ccc3c12] | 51 |
| 25 | 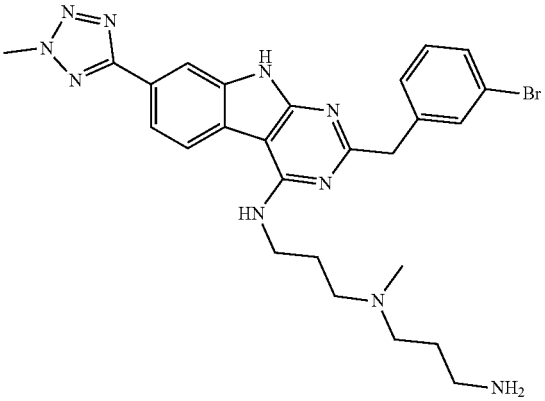 [SMILES: CN(CCCN)CCCNc1nc(Cc2cccc(Br)c2)nc2[nH]c3cc(-c4nnn(C)n4)ccc3c12] | 115 |

-continued

| | Structure | *EC$_{50}$ |
|---|---|---|
| 26 | 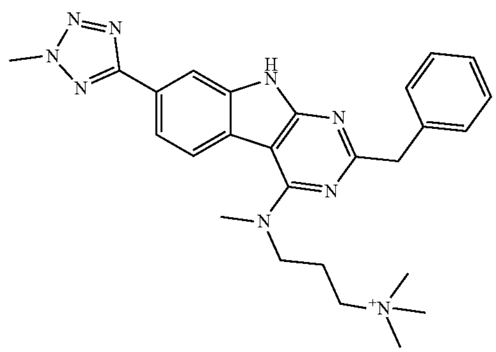 [SMILES: CN(CCC[N+](C)(C)C)c1nc(Cc2ccccc2)nc2[nH]c3cc(-c4nnn(C)n4)ccc3c12] | 484 |
| 27 | 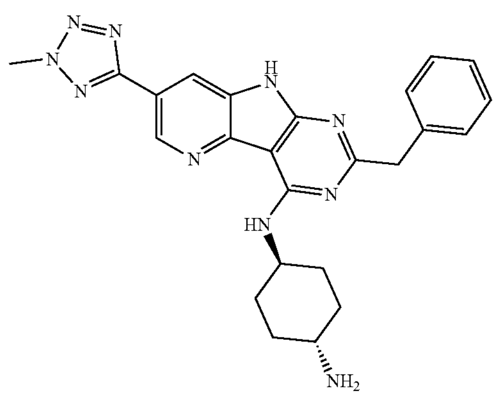 [SMILES: Cn1nnc(-c2cnc3c(c2)[nH]c2nc(Cc4ccccc4)nc(N[C@H]4CC[C@H](N)CC4)c23)n1] | 367 |
| 28 | 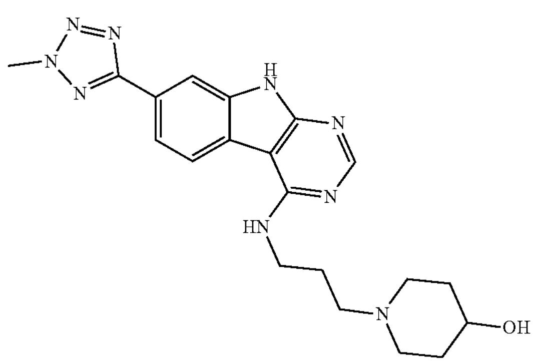 [SMILES: Cn1nnc(-c2ccc3c(c2)[nH]c2ncnc(NCCCN4CCC(O)CC4)c23)n1] | 277 |
| 29 | 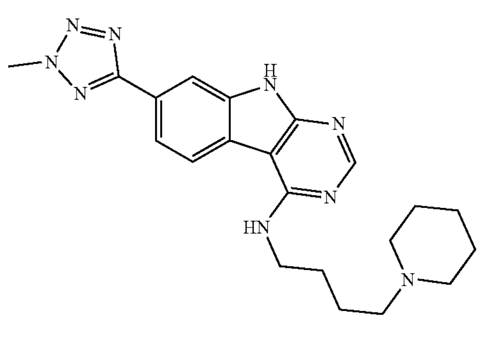 [SMILES: Cn1nnc(-c2ccc3c(c2)[nH]c2ncnc(NCCCCN4CCCCC4)c23)n1] | 36 |

-continued

| | Structure | *EC$_{50}$ |
|---|---|---|
| 30 | 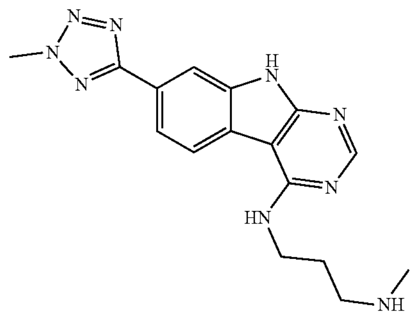 | 135 |
| 31 | 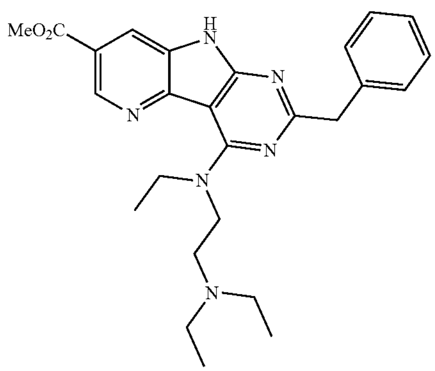 [SMILES: CCN(CC)CCN(CC)c1nc(Cc2ccccc2)nc2[nH]c3cc(C(=O)OC)cnc3c12] | 394 |
| 32 | 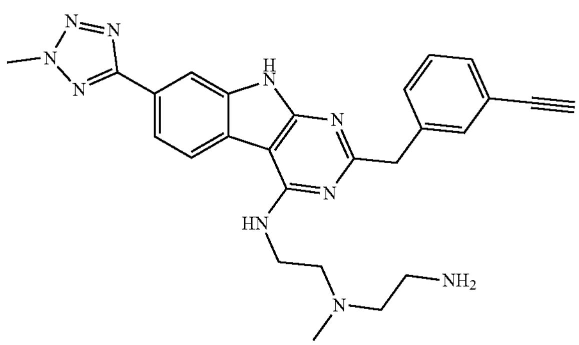 [SMILES: C#Cc1cccc(Cc2nc(NCCN(C)CCN)c3c(n2)[nH]c2cc(-c4nnn(C)n4)ccc23)c1] | 104 |
| 33 | 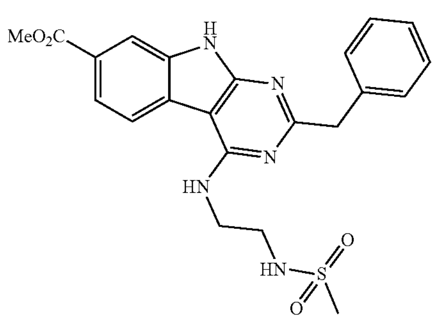 [SMILES: COC(=O)c1ccc2c(c1)[nH]c1nc(Cc3ccccc3)nc(NCCNS(C)(=O)=O)c12] | 33 |

-continued

| | Structure | *EC$_{50}$ |
|---|---|---|
| 34 | 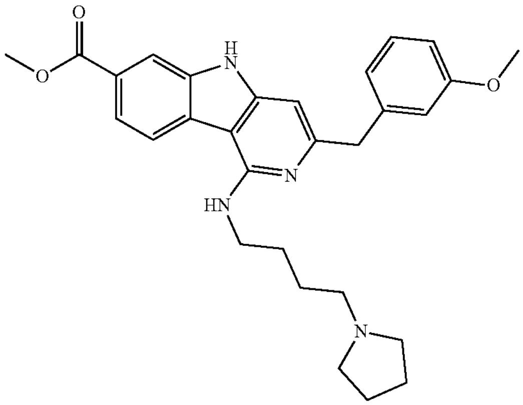 | 76 |
| 35 | 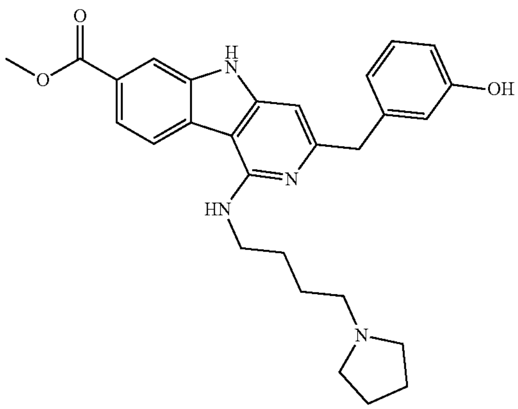 [SMILES: COC(=O)c1ccc2c(c1)[nH]c1cc(Cc3cccc(O)c3)nc(NCCCCN3CCCC3)c12] | 44 |
| 36 | 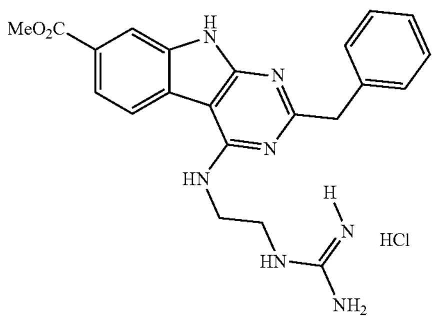 [SMILES: [H]/N=C(/N)NCCNc1nc(Cc2ccccc2)nc2[nH]c3cc(C(=O)OC)ccc3c12 ; Cl] | 68 |
| 37 | 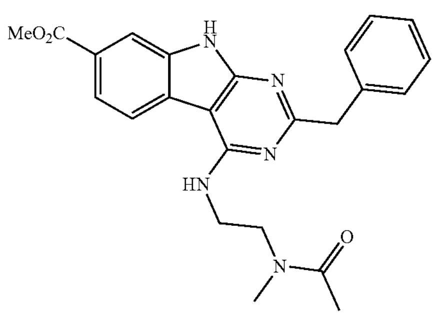 [SMILES: COC(=O)c1ccc2c(c1)[nH]c1nc(Cc3ccccc3)nc(NCCN(C)C(C)=O)c12] | 83 |

-continued
| | Structure | *EC$_{50}$ |
|---|---|---|
| 38 | 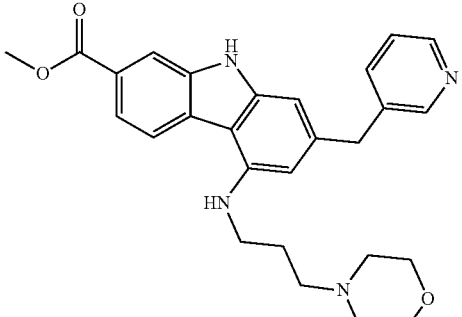 | 704 |
| 39 | 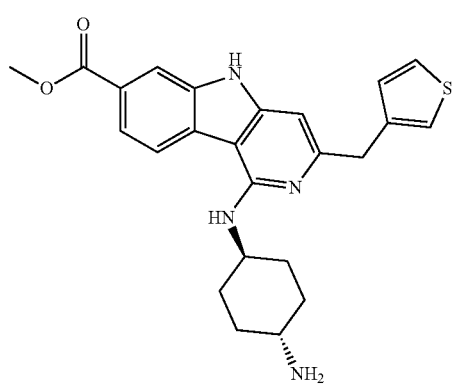 [SMILES: COC(=O)c1ccc2c(c1)[nH]c1cc(Cc3ccsc3)nc(N[C@H]3CC[C@H](N)CC3)c12] | 114 |
| 40 | 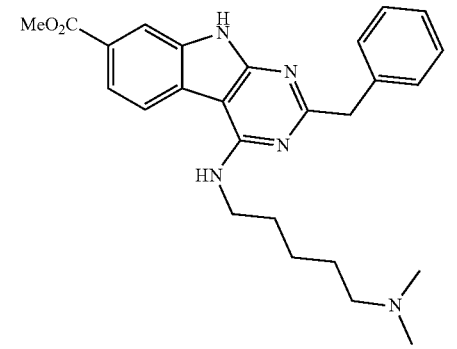 [SMILES: COC(=O)c1ccc2c(c1)[nH]c1nc(Cc3ccccc3)nc(NCCCCCN(C)C)c12] | 2.0 |
| 41 | 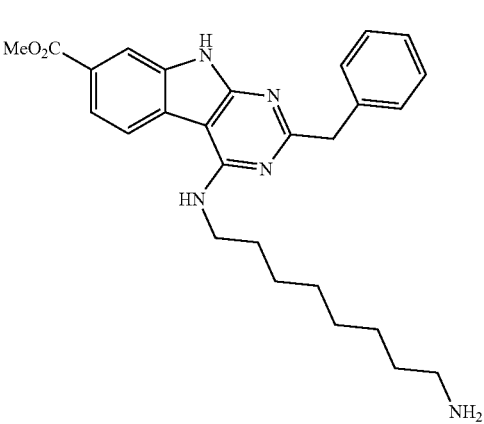 [SMILES: COC(=O)c1ccc2c(c1)[nH]c1nc(Cc3ccccc3)nc(NCCCCCCCCN)c12] | 39 |

-continued
| | Structure | *EC$_{50}$ |
|---|---|---|
| 42 | 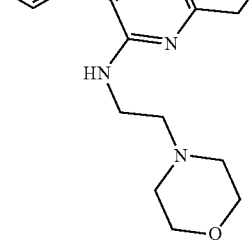 | 12.0 |
| 43 | 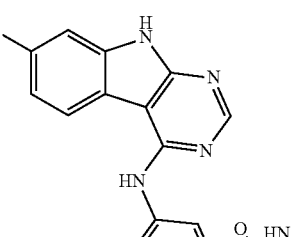 | 263 |
| 44 | 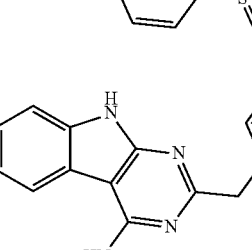 | 59 |
| 45 | 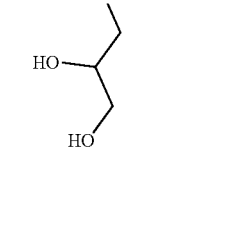 | 336 |

-continued

| | Structure | *EC$_{50}$ |
|---|---|---|
| 46 | 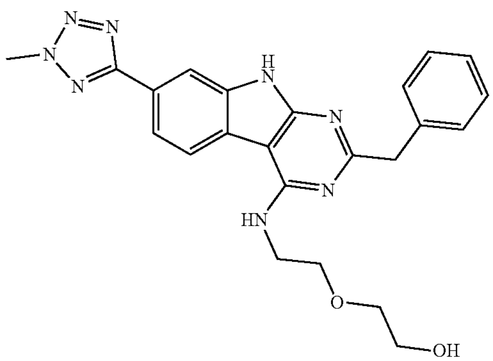 [SMILES: Cn1nnc(-c2ccc3c(c2)[nH]c2nc(Cc4ccccc4)nc(NCCOCCO)c23)n1] | 141 |
| 47 | 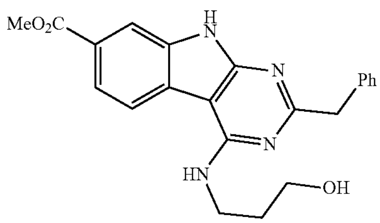 [SMILES: COC(=O)c1ccc2c(c1)[nH]c1nc(Cc3ccccc3)nc(NCCCO)c12] | 26 |
| 48 | 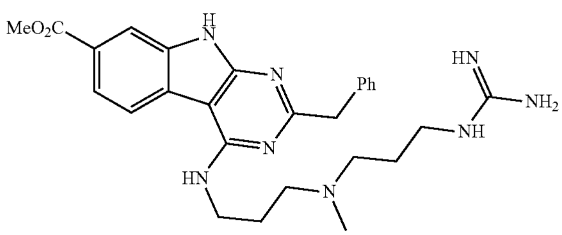 [SMILES: COC(=O)c1ccc2c(c1)[nH]c1nc(Cc3ccccc3)nc(NCCCN(C)CCCNC(=N)N)c12] | 61 |
| 49 | 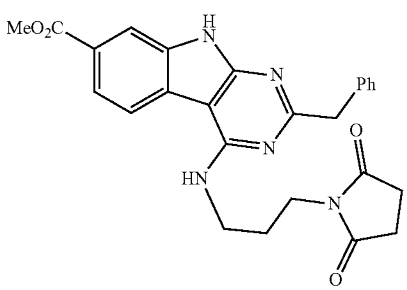 [SMILES: COC(=O)c1ccc2c(c1)[nH]c1nc(Cc3ccccc3)nc(NCCCN3C(=O)CCC3=O)c12] | 41 |
| 50 | 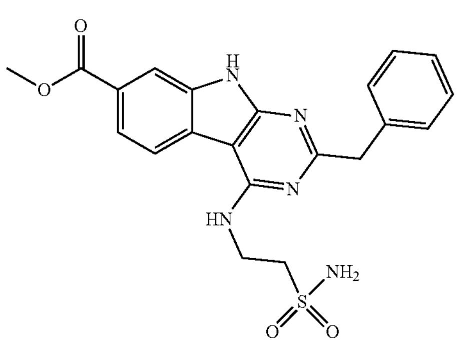 [SMILES: COC(=O)c1ccc2c(c1)[nH]c1nc(Cc3ccccc3)nc(NCCS(N)(=O)=O)c12] | 67 |

-continued

| | Structure | *EC$_{50}$ |
|---|---|---|
| 51 | 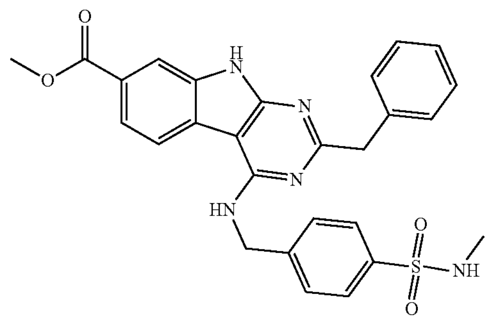 | 62 |
| 52 | 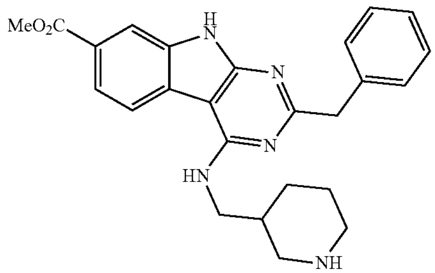 [SMILES: COC(=O)c1ccc2c(c1)[nH]c1nc(Cc3ccccc3)nc(NCC3CCCNC3)c12] | 7.0 |
| 53 | 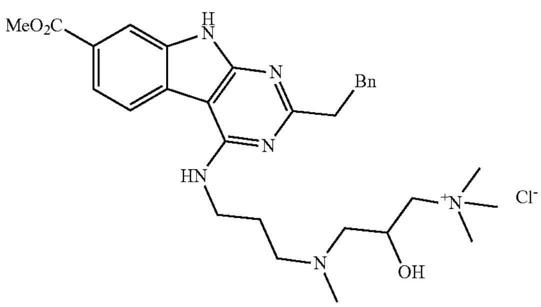 [SMILES: COC(=O)c1ccc2c(c1)[nH]c1nc(CCc3ccccc3)nc(NCCCN(C)CC(O)C[N+](C)(C)C)c12 ; [Cl-]] | 117 |
| 54 | 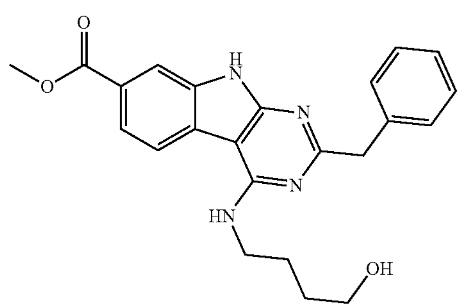 [SMILES: COC(=O)c1ccc2c(c1)[nH]c1nc(Cc3ccccc3)nc(NCCCCO)c12] | 118 |
| 55 | 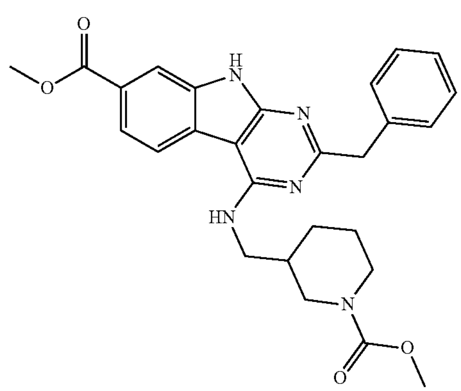 [SMILES: COC(=O)c1ccc2c(c1)[nH]c1nc(Cc3ccccc3)nc(NCC3CCCN(C(=O)OC)C3)c12] | 79.0 |

-continued

| | Structure | *EC$_{50}$ |
|---|---|---|
| 56 | 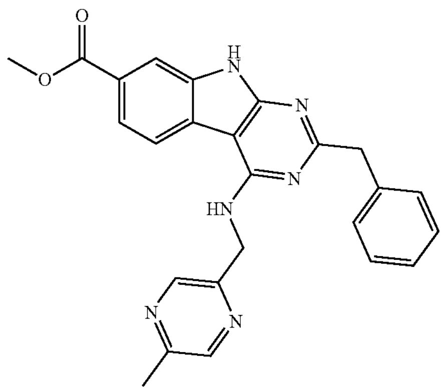 [SMILES: COC(=O)c1ccc2c(c1)[nH]c1nc(Cc3ccccc3)nc(NCc3cnc(C)cn3)c12] | 48 |
| 57 | 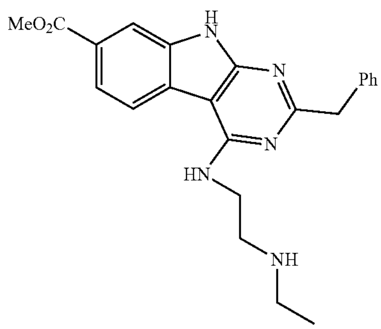 [SMILES: CCNCCNc1nc(Cc2ccccc2)nc2[nH]c3cc(C(=O)OC)ccc3c12] | 4.8 |
| 58 | 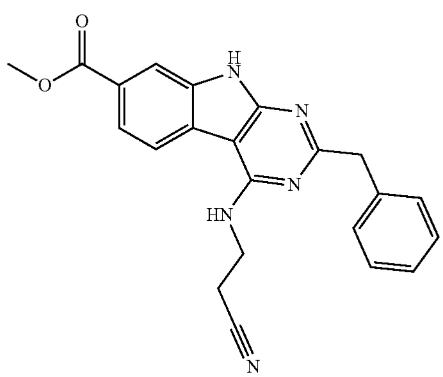 [SMILES: COC(=O)c1ccc2c(c1)[nH]c1nc(Cc3ccccc3)nc(NCCC#N)c12] | 79 |
| 59 | 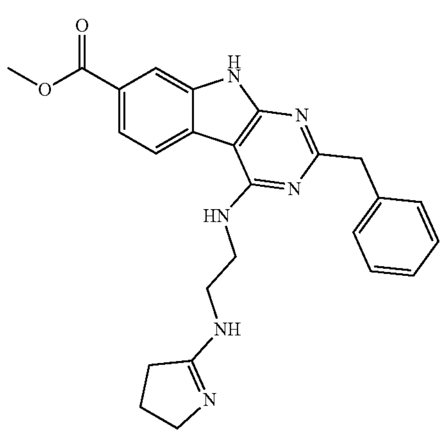 [SMILES: COC(=O)c1ccc2c(c1)[nH]c1nc(Cc3ccccc3)nc(NCCNC3=NCCC3)c12] | 75 |

-continued

| Structure | *EC$_{50}$ |
|---|---|
| 60 (structure with methyl ester, carbazole-pyrimidine core, benzyl, HN-NH-phenyl-SO$_2$Me) | 23 |
| 61 MeO$_2$C-...-Ph, HN-CH$_2$CH$_2$-N(iPr)$_2$ | 10.1 |

*EC$_{50}$ refers to the concentration of compound necessary to expand 50% more of CD34 + CD45RA- cells as compared to cells treated with DMSO.

UM171 in the fed-batch system led to significant expansion of CD34$^+$CD45RA$^-$ cells, an important subpopulation which encompasses all HSCs, including long-term (determined by their capacity to reconstitute NSG mice 20 to 30 weeks after transplantation) and short-term repopulating cells such as the CFU-GEMM (colony forming unit-granulocyte, erythrocyte, monocyte and megakaryocyte) progenitors which determine time to neutrophil engraftment. The CD34+CD45RA$^-$ and not CD34$^+$ phenotype represents the best surrogate parameter to monitor HSC expansion. Cells undergoing expansion in the fed-batch system with DMSO differentiate into mature cells losing CD34$^+$ expression from 100% to less than 10% after 12 days.

Figure 2:
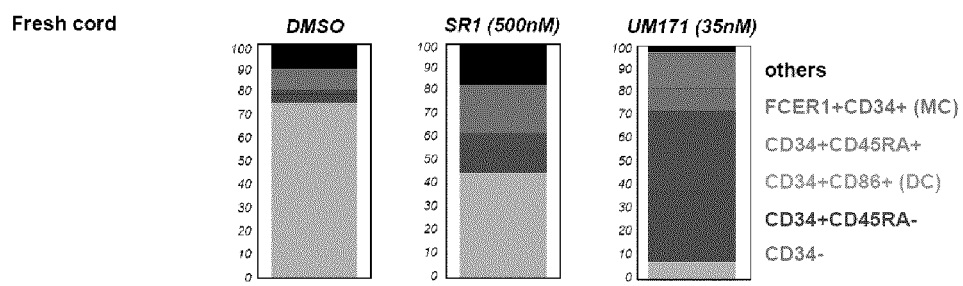
FIG. 2 illustrates cell populations identified in cord blood samples expanded and cultured with DMSO, SR1 or UM171, showing the unique signature of the graft.

As seen in FIG. 1, when human CD34+ progenitors were purified from cord blood samples and cultured for two weeks with UM171, said compounds promotes the ex vivo enrichment of primitive dendritic cell progenitors and compared to SR1 for example, results in a new graft (FIG. 2). The cell populations expanded and generated upon exposure to other molecules (like SR1) are different than those obtained with UM171. The dendritic cells population (CD86+CD34+) represent 40-50% of the graft in UM171 expanded cord blood while it represent less than 5% in SR1 expanded cord blood, and are not detectable in fresh cord blood. UM171 treatment dramatically changed graft composition leading to a 500-fold increase in immature dendritic cells. Mast cells expressing the FceR1A and c-Kit were also preferentially amplified by UM171 exposure and represented approximately 10% of the graft (>8000-fold expansion).

The ability to expand short- and long-term HSCs to unprecedented levels (>1000× expansion) with UM171/fed-batch lead to prompt and durable engraftment. The safety, feasibility, engraftment and immune reconstitution in patients is described herein.

Figure 3:
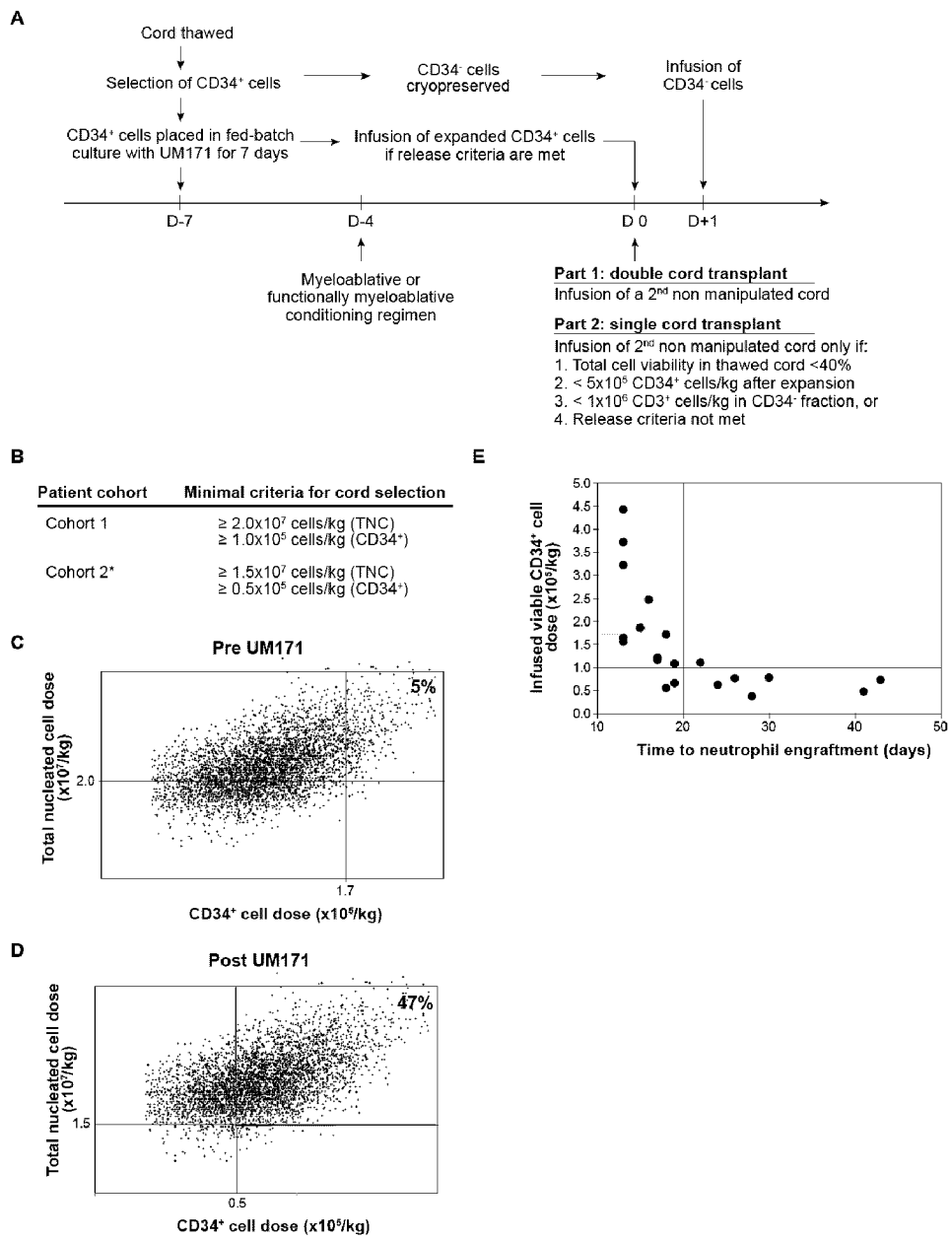
FIG. 3 illustrates in (A) the clinical trial design; in (B) the definition of patient cohort; cord blood accessibility using standard selection criteria for a 70 Kg patient in (C) or criteria used for cohort 2 patients in (D); and in (E) the historical data at Hôpital Maisonneuve-Rosemont showing relationship between CD34 cell dose (post thaw of CB unit) versus time to neutrophil engraftment.

In a 22 patients cohort, the capacity of expanded CB units using UM171/fed-batch system to result in durable engraftment with neutrophil recovery <21 days was tested. Dose reduction proceeded according to Wald test based on Cox modeling which takes into consideration the strong correlation between infused CD34$^+$ dose and neutrophil recovery within the clinically acceptable 21-day time point. For safety reasons, a minimum of i) 5×10$^5$/kg viable CD34$^+$ cells and ii) 1×10$^6$/kg viable CD3$^+$ T cells must be infused. Failure to achieve these values or to meet release criteria resulted in the injection of a second CB (FIG. 3A).

Cohort description and pre expansion CB selection criteria are as follows:
Cohort 1: TNC≥2.0×10$^7$/kg and CD34$^+$≥1.0×10$^5$/kg;
Cohort 2: TNC≥1.5×10$^7$/kg and CD34$^+$≥0.5×10$^5$/kg; and
Cohort 3: TNC≥1.25×10$^7$/kg and CD34$^+$≥0.25×10$^5$/kg.
To move from cohort 1 to cohort 2, a minimum of 3 patients had to engraft within 18 days following infusion of a single UM171-expanded CB that had <2.0×10$^5$ CD34+ cells/kg at thaw. To move from cohort 2 to cohort 3, a minimum of 3 patients had to engraft within 18 days following infusion of a single UM171-expanded CB that had <1.0×10$^5$ CD34+ cells/kg at thaw (FIG. 3B). Cohort 2 made 47% of banked CB units available, compared to only 5% when unexpanded CB are used (FIGS. 3C and 3D).

Based on the strong relationship between neutrophil engraftment and infused viable CD34$^+$ dose, one can extrapolate within a small cohort of patients if CD34$^+$ cell dose reduction is safely achievable clinically. For example, viable CD34$^+$ cell dose above 3×10$^5$/kg predicts very rapid engraftment, whereas levels below 0.5×10$^5$/kg lead to late engraftment (FIG. 3E).

Henceforth, 22 patients (numbered 1-22) received a single UM171 cord (N=22). Median follow-up is 18 months (range 1-28 months for patients 1-22). Results were compared to same institution continuous transplanted patients with unmanipulated cord blood (Ctrl CB). Infusion of ≥1×10$^5$ viable CD34$^+$ cells/kg was effected as this ensured neutrophil engraftment within 21 days (FIG. 3E). In addition, only CB controls who received the same conditioning regimen without ATG as patients in the current trial were included in the control group.

The CB selection process was standardized to avoid any variability. The CB selected for the study were compared to CB(s) selected if patient were not on protocol. This allowed demonstration of improvement in HLA match and decrease in need for double CBs.

CB for expansion were purchased and shipped to manufacturing center (FHCRC for 1$^{st}$ 10 patients and CETC for the next 15 patients). The CB were thawed and underwent CD34$^+$ cell selection; the CD34$^+$ cells were cultured in the fed-batch for 7 days with growth factors, then washed and cryopreserved were shipped to the transplant center. The CD34$^-$ cells were cryopreserved and infused to the patient at transplant. All cell products were assessed for viability and phenotype at every step and release criteria include sterility, mycoplasma, endotoxin, minimal 10 fold CD34+ expansion and viability>70%.

Patients received a predefined myeloablative conditioning regimen (Barker et al., 2005, Blood, 105: 1343-1347; Oran et al., 2001, Biology of blood and marrow transplantation: Journal of the American Society for Blood and Marrow Transplantation, 17: 1327-1334). On the day of transplant, expanded CB were infused, while CD4-product was infused the next day. GVHD prophylaxis consisted of mycophenolate mofetil and cyclosporine. Patients are followed for a minimum of 3 years to ensure the absence of any unexpected complication. Patients are receiving standardized supportive care.

As can been seen in Table 1 below, cells population were measured at day 14, 21, 28, 56, 100, at 6 months and 12 months post transplantation of the graft. Antibodies panels were chosen to be measured to allow the evaluation of both myeloid and lymphoid lineages engraftment. Particularly:

—CD45$^+$CD3$^+$ are lymphoid T cells

—CD56$^+$NKP46$^+$ or NKG2A$^+$ are known NK cells.

Table 1 express the number of cells measured per µl of blood µl/blood±5%.

TABLE 1

Expansion of NK cells measured in patient after cord blood transplant expanded with UM171

| Average of all Patients (µl/blood ± 5%) | J14 | J21 | J28 | J56 | J100 | M6 | M12 |
| --- | --- | --- | --- | --- | --- | --- | --- |
| CD45+ CD3+ | 0.1159 | 0.0773 | 0.1208 | 0.8568 | 0.9113 | 1.0792 | 2.5205 |
| Activated CD3+ | 0.0014 | 0.0023 | 0.0021 | 0.0631 | 0.0261 | 0.0102 | 0.0247 |
| CD3+ CD117+ | 0.0157 | 0.0010 | 0.0019 | 0.0163 | 0.0111 | 0.0082 | 0.0098 |
| CD3+ FCER1+ | 0.0257 | 0.0003 | 0.0006 | 0.0094 | 0.0031 | 0.0027 | 0.0033 |
| CD3+ NKG2A+ | 0.0307 | 0.0045 | 0.0040 | 0.0283 | 0.0164 | 0.0248 | 0.0681 |
| CD45+ CD3− | 0.6191 | 0.9127 | 2.5961 | 9.0384 | 7.3954 | 5.6145 | 3.5695 |
| Activated CD45+ CD3− | 0.0025 | 0.0133 | 0.0344 | 0.1120 | 0.0676 | 0.1011 | 0.0560 |
| CD16/56− NKP46− | 0.3336 | 0.3959 | 1.0043 | 5.9586 | 4.4629 | 2.9746 | 2.4824 |
| CD16/56+ NKP46+ | 0.0672 | 0.1912 | 0.6216 | 1.4386 | 1.0450 | 0.5541 | 0.3086 |
| CD16/CD56− NKP46+ | 0.0168 | 0.0610 | 0.0892 | 0.1516 | 0.0476 | 0.0289 | 0.0190 |
| NK cells | 0.0643 | 0.1938 | 0.5967 | 1.2330 | 0.8180 | 0.4652 | 0.2640 |
| Immature cells (Prog. CD117+) | 0.0737 | 0.0650 | 0.0972 | 0.8225 | 0.8097 | 0.9186 | 0.0647 |
| Inflammation APC (FCER1+) | 0.0080 | 0.0034 | 0.0116 | 0.0671 | 0.0719 | 0.0898 | 0.0557 |
| Neutrophil/macrophage/mastocyte | 0.2136 | 0.3059 | 0.9172 | 1.5991 | 1.8399 | 2.0569 | 0.7595 |
| CD45+ CD3− NKG2A+ | 0.0895 | 0.2119 | 0.6372 | 1.3776 | 0.9513 | 0.7242 | 0.5500 |
| Nb CD45+ acquired | 94438 | 112353 | 117663 | 80936 | 74282 | 142387 | 162494 |
| TOTAL µl/blood | 0.1567 | 0.4031 | 1.2588 | 2.8162 | 1.9962 | 1.2783 | 0.8586 |

Figure 4:
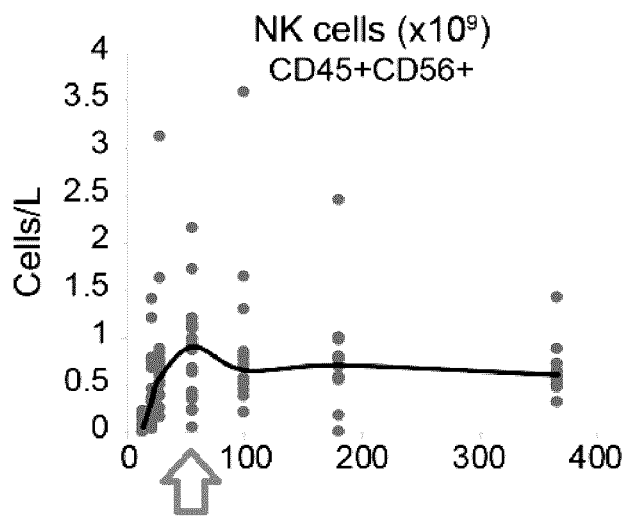
FIG. 4 illustrates post-engraftment measurement of NK cells in UM171 CB patients wherein the arrow points to measurement at about 2 months post-transplant.

As seen, a flare or expansion of NK cells was measured in vivo in patients between day 21 and coming back to initial numbers at 12 months post transplantation. As seen in FIG. 4, the expansion of NK cells measured in patients is significantly higher at two months post-engraftment (see arrow in FIG. 4) than what has been reported (see Lucchini et al., 2015, Cytotherapy, 17: 711-722).

When CD11c$^+$CD14$^+$ and CD11c$^+$CD14$^-$ cells levels were measured, which are two subsets of dendritic cells, a similar flare or expansion is observed (Table 2).

TABLE 2

Expansion of DC cells measured in patients cord blood transplant expanded with after UM171

| Average of all Patients (µl/blood ± 5%) | J14 | J21 | J28 | J56 | J100 | M6 | M12 |
| --- | --- | --- | --- | --- | --- | --- | --- |
| CD45+/singlet2 | — | — | — | — | — | — | — |
| CD45+ CD3+ | 0.14 | 0.07 | 0.12 | 0.72 | 0.87 | 1.33 | 2.67 |
| CD45+ CD3− | 0.60 | 0.92 | 2.59 | 9.18 | 7.44 | 5.37 | 3.42 |
| CD11c− CD14− | 0.21 | 0.35 | 0.92 | 3.88 | 4.12 | 3.00 | 2.42 |
| CD11c− CD14+ | 0.30 | 0.36 | 1.00 | 3.01 | 0.43 | 0.55 | 0.17 |

TABLE 2-continued

Expansion of DC cells measured in patients cord blood transplant expanded with after UM171

| Average of all Patients (μl/blood ± 5%) | J14 | J21 | J28 | J56 | J100 | M6 | M12 |
| --- | --- | --- | --- | --- | --- | --- | --- |
| CD11c+ CD14− | 0.01 | 0.04 | 0.06 | 0.29 | 0.55 | 0.63 | 0.31 |
| CD11c+ CD14+ | 0.0819 | 0.1611 | 0.6136 | 1.9942 | 2.3338 | 1.3920 | 0.5140 |
| HLA− DR+ | 0.01 | 0.02 | 0.03 | 1.04 | 1.44 | 1.10 | 1.57 |
| pDC (CD123+ BDCA2+) | 0.00 | 0.00 | 0.01 | 0.03 | 0.01 | 0.01 | 0.02 |
| pDC CD86 low/int | 0.00 | 0.00 | 0.00 | 0.01 | 0.00 | 0.00 | 0.00 |

The in vivo flare in natural killer cells and dendritic cells measured in patients transplanted with UM171 expanded cells have an immunosuppressive activity and prevent GVH reaction and allow graft tolerance. The immune cell recovery is faster with UM171 expanded cord, which is important for decreasing post-hematopoietic cell transplant (post-HCT) infections and relapse. Accordingly, UM171 promotes the expansion of HSCs and of progenitor cells by coordinating pro- and anti-inflammatory responses and help controlling the inflammatory state.

Figure 5:
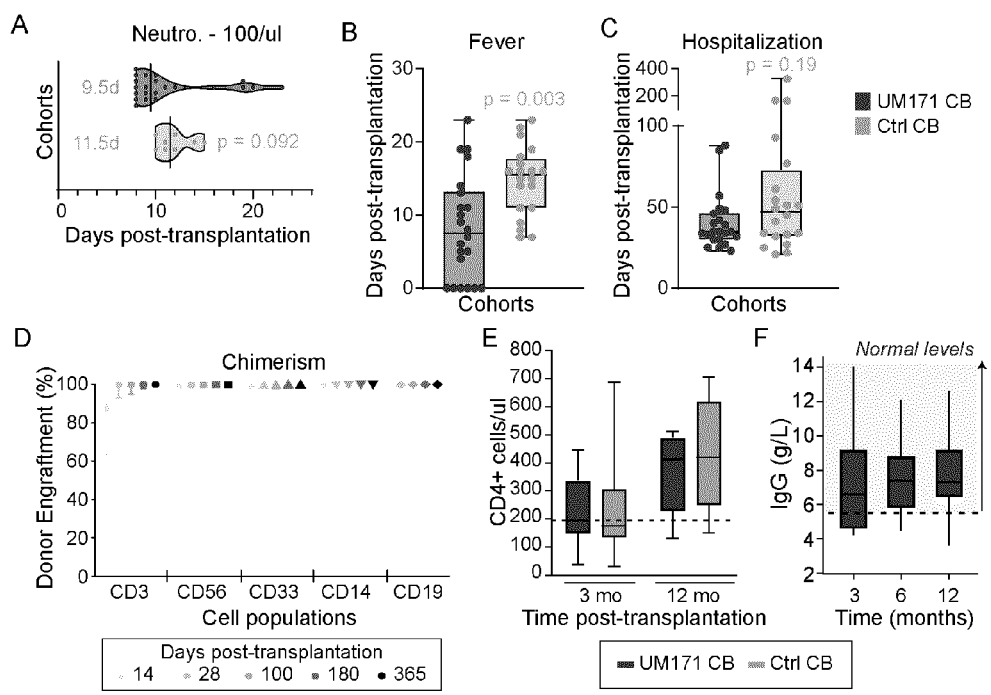
FIG. 5 illustrates engraftment and chimerism, showing in (A) time to 100 neutrophil engraftment; (B) resolution of fever and (C) duration of hospitalization for patients transplanted with UM171-expanded CB (blue) or unmanipulated CB cells (green). (D) Lineage chimerism at different time points in days in patients transplanted with UM171-expanded CB cells. (E) Comparison of CD4 counts at 3 and 12 months in patients transplanted with UM171 expanded CB and unmanipulated CB. (F) IgG levels in recipients of UM171 expanded CB. Ctrl CB: unmanipulated cord blood.

Cumulative incidence of neutrophil recovery was 100% with a median time to 100 and 500 neutrophils of 9.5 (8-23) and 18 (10-30) days, respectively (FIG. 5A). Median time to 100 neutrophils for Ctrl CB was 11.5 days, while time to 500 neutrophils was 19 days. Interestingly, achieving 100 neutrophils was independent of CD34 cell dose. No late graft failure developed and almost all patients had platelets ≥100, neutrophils ≥21500 and hemoglobin ≥100 at 6 and 12 months post-transplant. Prompt engraftment resulted in faster resolution of fever post-transplantation and shorter hospitalization time for UM171 patients (FIGS. 5B and 5C).

Chimerism analysis of different cell populations, notably CD3, CD56, CD19, CD14, and CD33 revealed that patients rapidly achieved 100% donor engraftment in all cell lines (FIG. 5D).

After more than 10 months of follow-up, it is reported that out of 16 patients, only 2 patients with grade III acute GVHD was observed (which promptly responded to steroids) and no case of moderate to severe chronic GVHD was observed. Interestingly, few viral infectious complications (CMV, EBV, adenovirus cystitis for example) was observed indicating a robust immune response in these patient. A spontaneous resolution of EBV viremia was observed in 2 out of 3 patients which were infected prior to the transplantation (Table 3).

TABLE 3

Spontaneous resolution of EBV viremia in patients

|  | Patient 6 | Patient 9 | Patient 12 |
| --- | --- | --- | --- |
| 1st positive EBV viremia | 30,000 | 15,488 | 33,113 |
| Day of 1st dose rituximab | 0 | 4,266 | 190,546 |
| Day of 2nd dose rituximab | 0 | 427 | 0 |

Threshold of rituximab therapy is 10,000 copies

Accordingly, 11 patients were positive for CMV serology and 6 developed viremia requiring therapy but no case of CMV disease occurred. Two cases of early onset adenovirus cystitis occurring prior to D+25 required therapy with intravenous cidofovir. Three patients received rituximab for EBV viremia. There was no case of PTLD. Two cases of *Pneumocystis jiroveci* pneumonia (PJP) occurred, the first patient was non-compliant with prophylaxis for >2 months and the second was on atovoquone prophylaxis in an institution where atovaquone resistant PJP is present. There were 2 cases of dermatomal shingles, both while off prophylaxis. No case of invasive fungal infection, toxoplasmosis, or HHV6 infection was ascertained. Median CD4/μL at 3, 6 and 12 months were 196, 301 and 413, respectively (FIG. 5E). Only 1 patient did not achieve a CD4 count of 50 by D+100. Median IgG at 3, 6, 12 months were 5.9, 7.3 and 7.3 g/L, respectively (Normal 5.5-16.3) (FIG. 5F).

Figure 6:
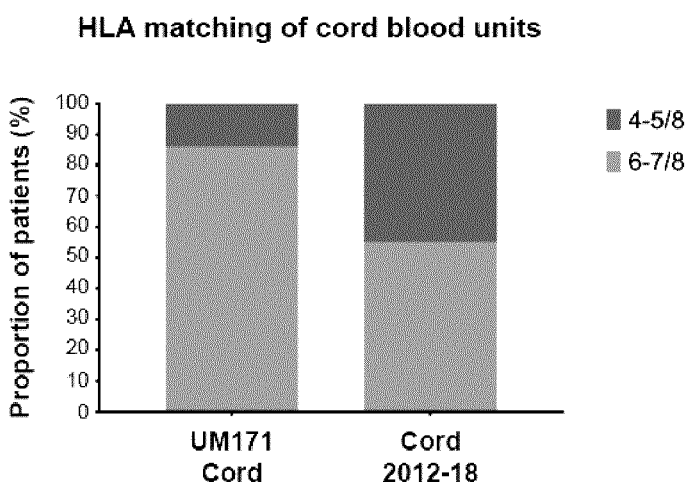
FIG. 6 illustrates HLA matching of CB blood units in UM171 patient cohort (left) and in contemporary CB cohort (right), showing 6⅞ match between patient and CB unit: 4⅝ match.

When compared to standard selection criteria for cord blood (TNC≥2.0×10$^7$/kg and CD34≥1.7×10$^5$/kg), 12/22 patients got a better HLA matched cord as minimal cell dose criteria was lower. Thus >75% of the patients were transplanted with a CB HLA matched 6⅞ (5⅝, 15⅝, 2⅞) (FIG. 6). No patient was excluded from the trial because a HLA matched CB with sufficient cell dose could not be identified.

Figure 7:
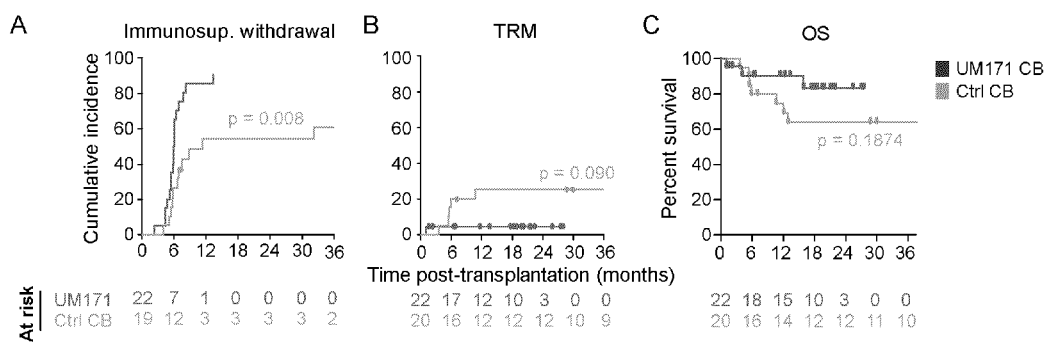
FIG. 7 illustrates cumulative incidence of (A) immunosuppressor withdrawal, (B) transplant-related mortality (TRM); and (C) Kaplan-Meier estimates of overall survival (OS) in UM171-expanded CB and unmanipulated CB cohorts.

At 12 months post-transplant, immunosuppressive therapy had been discontinued in 85% of UM171 CB vs 72% of Ctrl CB patients (FIG. 7A). Overall, 1 patient has died of diffuse alveolar hemorrhage, for a cumulative incidences of TRM at 1 one year of 5% (95% CI: 1-31%) in UM171 CB cohort compared to 25% (95% CI: 12-54) in Ctrl CB cohort (FIG. 7B). OS at 12 months was 90% (95% CI: 67-98), compared to 75% (95% CI: 49-87) in Ctrl CB (FIG. 7C).

It is demonstrated herein that transplanting patients with a single, smaller, better HLA matched UM171 expanded CB would lower the risk of morbidity and mortality of CB transplantation. To achieve this goal, a phase 1-11 clinical trial was conducted and primary endpoints of feasibility (expansion failure 1 cord with suspicion of inherent underlying abnormality), safety with 5% TRM, and capability of using smaller, better HLA matched cords with prompt engraftment was demonstrated.

Furthermore, prompt (<D+18), robust and durable neutrophilic engraftment was ensured without any graft failure. Furthermore, very early recovery of 100 neutrophils (D+10) was achieved leading to rapid resolution of febrile neutropenia (D+7.5) and shorter hospitalization (35 days for UM171 CB vs 47 days for CB controls), similar to that seen with conventional allogeneic transplants (29.5 days for BM and 33 days for PB). One would expect an earlier discharge for UM171 patients compared to BM-PB because of prompter 500 neutrophil recovery.

Cord blood is traditionally thought to be associated with poor and delayed T cell immune reconstitution at least in part due to the naivety of the infused T cells and lack of memory T cells contributing to an increased risk of viral infections. Despite lack of transfer of memory T cells and an average T cell loss of 33% with the described expansion procedure, CD4 recovery is at least as fast compared to unmanipulated CB transplant (FIG. 4E). CD4 recovery has been shown to be important not only for prevention of infectious complications but also TRM and relapse. In pediatric CB transplantation, Admiral et al. (2016, Blood, 128: 2734-2741) reported that if a CD4 count of 50 is not achieved by D+100, the risk of relapse was 100% for AML (vs. 24%), TRM 31% (vs. 11%), and OS 56% (vs. 73%). In the cohort of 22 patients described herein, only one had not achieved a CD4 of 50 by D+100. Prompt immune recovery in the trial translated in absence of severe viral infections with no CMV disease or PTLD. Furthermore, ⅔ patients who were treated for EBV viremia had already improved EBV titers below threshold before receiving rituximab.

Expected TRM in CB transplantation is higher than with conventional transplants because of slower neutrophil and immune reconstitution, and higher risk of graft failure. The high TRM and the prolonged hospitalizations are the main reasons for the declining interest in CB and the rise of use of haploidentical transplants. The HCT-Cl is the best validated index to predict TRM in transplantation. TRM with CB is reported at 26% and 50% if HCTCl is <3 and >3, respectively. Median HCT-Cl in the trial was 2 with 8 (38%) patients having a score 23. The TRM thus appears to be very low at 5%. There are multiple reasons to explain and corroborate a low TRM: i) rapid neutrophil recovery at D+18 with very rapid attainment of 100 neutrophils, ii) better HLA match with >75% of patients receiving a ≥⅝ allele matched CB, iii) very low risk of graft failure, iv) absence of ATG use, v) prompt immune reconstitution leading to low risk of severe viral infections, and vi) absence of steroid refractory GVHD. It is unusual to have TRM with CB transplantation beyond 12 months because of the low incidence of chronic GVHD and therefore it is unlikely that the TRM described herein will increase dramatically with longer follow up.

In summary, excellent results were obtained with single UM171 expanded cord blood transplants in patients with high-risk hematologic malignancies and multiple comorbidities. Findings provided herein confirm UM171 expanded single CB as an acceptable graft when no HLA identical donor is available.

While the disclosure has been described in connection with specific embodiments thereof, it will be understood that it is capable of further modifications and this application is intended to cover any variations, uses, or adaptations, including such departures from the present disclosure as come within known or customary practice within the art and as may be applied to the essential features hereinbefore set forth, and as follows in the scope of the appended claims.

What is claimed is:

1. A method for reducing severe graft-versus-host disease (GVHD), relapse, and/or severe viral infections in a patient comprising the steps of:
   a) culturing a starting population of hematopoietic stem and/or progenitor cells (HSC) with at least one compound of formula I:

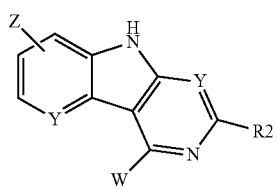

I or a salt or a prodrug thereof, wherein:
each Y is independently selected from N and CH;
Z is
—CN
—C(O)OR1,
—C(O)N(R1)R3,
—C(O)R1, or
heteroaryl optionally substituted with one or more RA or R4 substituents,
wherein, when (R1) and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
W is
—CN,
—N(R1)R3,
—C(O)OR1,
—C(O)N(R1)R3,
—NR1C(O)R1,
—NR1C(O)OR1,
—OC(O)N(R1)R3,
—OC(O)R1,
—C(O)R1,
—NR1C(O)N(R1)R3,
—NR1S(O)$_2$R1,
benzyl optionally substituted with 1, 2 or 3 RA or R1 substituents,
—X-L-(X-L)$_n$-N(R1)R3,
—X-L-(X-L)$_n$-heteroaryl optionally substituted with one or more RA or R4 substituents attached on either or both the L and heteroaryl groups,
—X-L-(X-L)$_n$-heterocyclyl optionally substituted with one or more RA or R4 substituents attached on either or both the L and heterocyclyl groups,
—X-L-(X-L)$_n$-aryl optionally substituted with one or more RA or R4 substituents,
—X-L-(X-L)$_n$-NR1RA or
—(N(R1)-L)$_n$-N$^+$R1R3R5 R6$^-$
wherein n is an integer equal to either 0, 1, 2, 3, 4, or 5, and wherein, when R1 and R3 are attached to a nitrogen atom, optionally they join together with the nitrogen atom to form a 3 to 7-membered ring which optionally includes one or more other heteroatom selected from N, O and S, optionally the ring is substituted with one or more RA or R4;
each X is independently selected from C, O, S, and NR1;
each L is independently
—C$_{1-6}$ alkylene,
—C$_{2-6}$ alkenylene,
—C$_{2-6}$ alkynylene,
—C$_{3-7}$cycloalkylene, which optionally includes one or more other heteroatom selected from N, O and S or
—C$_{3-7}$ cycloalkenylene, which optionally includes one or more other heteroatom selected from N, O and S
wherein the alkylene, the alkenylene, the alkynylene the cycloalkylene and the cycloalkenylene groups are each independently optionally substituted with one or two R4 or RA substituent;
R1 is each independently
—H,
—C$_{1-6}$ alkyl,
—C$_{2-6}$ alkenyl,
—C$_{2-6}$ alkynyl,
—C$_{3-7}$ cycloalkyl,
—C$_{3-7}$ cycloalkenyl,
—C$_{1-5}$ perfluorinated,
heterocyclyl,
aryl,
heteroaryl, or
benzyl, wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 RA or Rd substituents;

R2 is
- —H,
- —$C_{1-6}$ alkyl, optionally substituted with one more RA substituents
- —C(O)R4,
- -L-heteroaryl optionally substituted with one or more RA or R4 substituents
- -L-heterocyclyl optionally substituted with one or more RA or R4, or
- -L-aryl optionally substituted with one or more RA or R4 substituents;

R3 is each independently
- —H,
- —$C_{1-6}$ alkyl,
- —$C_{2-6}$ alkenyl,
- —$C_{2-6}$ alkynyl,
- —$C_{3-7}$ cycloalkyl,
- —$C_{3-7}$ cycloalkenyl,
- —$C_{1-5}$ perfluorinated,
- -heterocyclyl,
- -aryl,
- -heteroaryl, or
- -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R4 is each independently
- —H,
- —$C_{1-6}$ alkyl,
- —$C_{2-6}$ alkenyl,
- —$C_{2-6}$ alkynyl,
- —$C_{3-7}$ cycloalkyl,
- —$C_{3-7}$ cycloalkenyl,
- —$C_{1-5}$ perfluorinated,
- -heterocyclyl,
- -aryl,
- -heteroaryl, or
- -benzyl, wherein the alkyl, the alkenyl, the alkynyl, the cycloalkyl, the cycloalkenyl, the perfluorinated alkyl, the heterocyclyl, the aryl, the heteroaryl and the benzyl groups are each independently optionally substituted with 1, 2 or 3 RA or Rd substituents;

R5 is each independently
- —$C_{1-6}$ alkyl,
- —$C_{1-6}$ alkylene-$C_{2-6}$ alkenyl which optionally includes one or more other heteroatom selected from N, O and S
- —$C_{1-6}$ alkylene-$C_{2-6}$ alkynyl which optionally includes one or more other heteroatom selected from N, O and S
- -L-aryl which optionally includes one or more RA or R4 substituents
- -L-heteroaryl which optionally includes one or more RA or R4 substituents
- —$C_{1-6}$ alkylene-C(O)O—
- —$C_{1-6}$ alkylene-C(O)OR1
- —$C_{1-6}$ alkylene-CN
- —$C_{1-6}$ alkylene-C(O)NR1 R3, wherein R1 and R3 optionally they join together with the nitrogen atom to form a 3 to 7-membered ring which optionally includes one or more other heteroatom selected from N, O and S; or
- —$C_{1-6}$ alkylene-OH;

R6 is
- Halogen
- —OC(O)$CF_3$ or
- —OC(O)R1;

RA is each independently
- -halogen,
- —$CF_3$,
- —OR1,
- -L-OR1,
- —$OCF_3$,
- —SR1,
- —CN,
- —$NO_2$,
- —NR1 R3,
- -L-NR1R1,
- —C(O)OR1,
- —$S(O)_2$R4
- —C(O)N(R1)R3,
- —NR1C(O)R1,
- —NR1C(O)OR1,
- —OC(O)N(R1)R3,
- —OC(O)R1,
- —C(O)R4,
- —NHC(O)N(R1)R3,
- —NR1C(O)N(R1)R3, or
- —$N_3$; and Rd is each independently
- —H,
- —$C_{1-6}$ alkyl,
- —$C_{2-6}$ alkenyl,
- —$C_{2-6}$ alkynyl,
- —$C_{3-7}$ cycloalkyl,
- —$C_{3-7}$ cycloalkenyl,
- —$C_{1-5}$ perfluorinated
- -benzyl or
- -heterocyclyl;

optionally together with at least one cell expanding factor, b) expanding said cultured population of hematopoietic stem and/or progenitor cells (HSC) producing a graft; and c) transplanting said graft in said patient thereby reducing severe graft-versus-host disease (GVHD), relapse, and/or severe viral infections in said patient.

2. The method of claim 1, wherein the hematopoietic stem cells are from umbilical cord blood cells, mobilized peripheral blood cells, or bone marrow cells.

3. The method of claim 2, wherein the hematopoietic stem cells are from human cord blood cells.

4. The method of claim 1, wherein said expanded stem and/or progenitor cells are purified for CD34$^+$, CD38$^+$, CD90$^+$, CD45RA$^+$, CD133 and/or CD49f$^+$ cells.

5. The method of claim 4, wherein said CD34+ cells are EPCR+ cells.

6. The method of claim 1, wherein said starting population of hematopoietic stem and/or progenitor cells (HSC) are cultured with at least one cell expanding factor.

7. The method of claim 1, wherein said starting population of hematopoietic stem and/or progenitor cells (HSC) are further cultured with an aryl hydrocarbon receptor (AHR) antagonist.

8. The method of claim 7, wherein the AHR antagonist is Stem Regenin 1 (SR1) or CH223191.

9. The method of claim 1, wherein the compound of formula I is

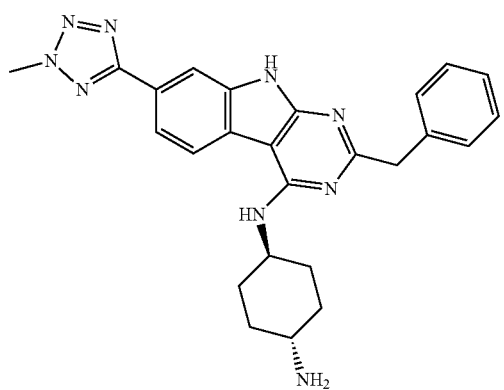 [SMILES: Cn1nnc(-c2ccc3c(c2)[nH]c2nc(Cc4ccccc4)nc(N[C@H]4CC[C@H](N)CC4)c23)n1]

or a pharmaceutically acceptable salt thereof.

10. The method of claim 1, wherein the compound of formula I is a hydrobromide salt of

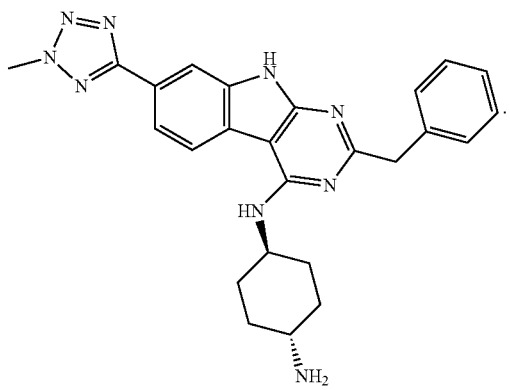 [SMILES: Cn1nnc(-c2ccc3c(c2)[nH]c2nc(Cc4ccccc4)nc(N[C@H]4CC[C@H](N)CC4)c23)n1]

11. The method of claim 1, wherein the compound of formula I is

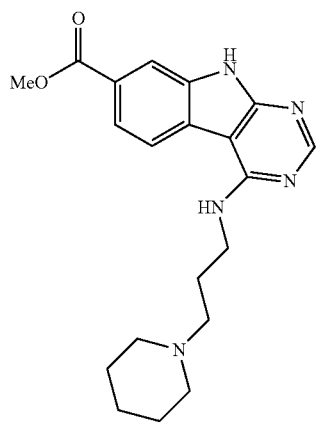 [SMILES: COC(=O)c1ccc2c(c1)[nH]c1ncnc(NCCCN3CCCCC3)c12]

or a pharmaceutically acceptable salt thereof.

12. The method of claim 1, wherein the compound of formula I is:

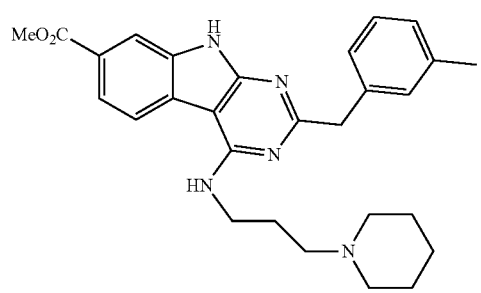

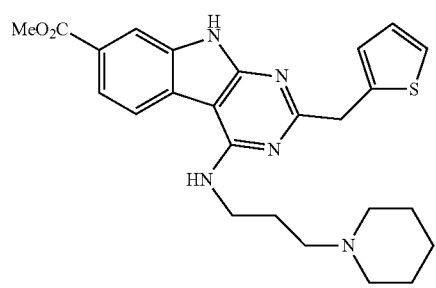

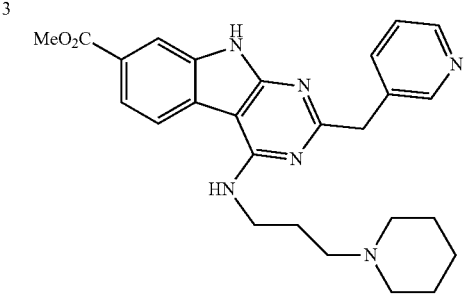

-continued
5
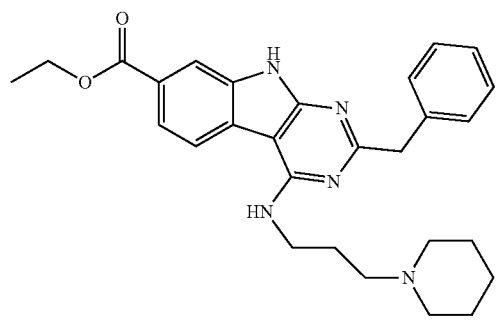
6
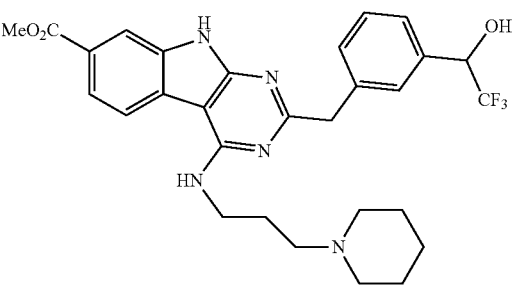
7
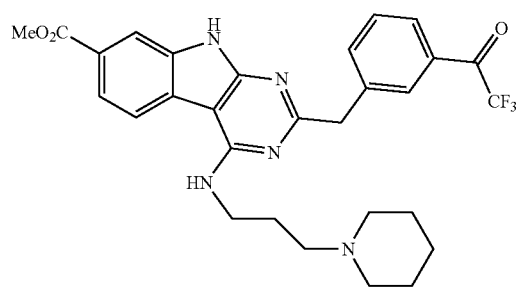
8
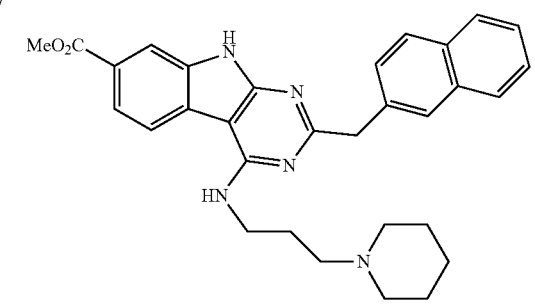
9
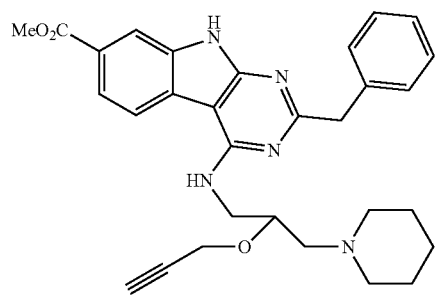
10
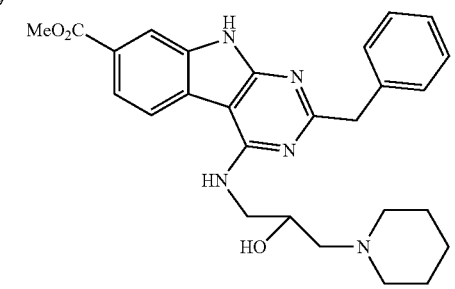
11
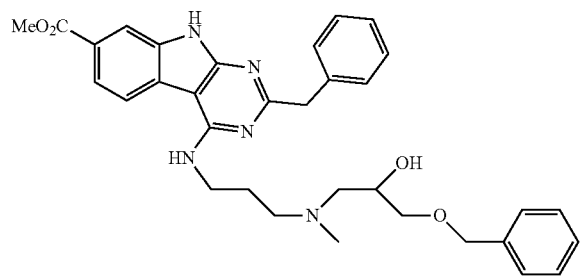
12
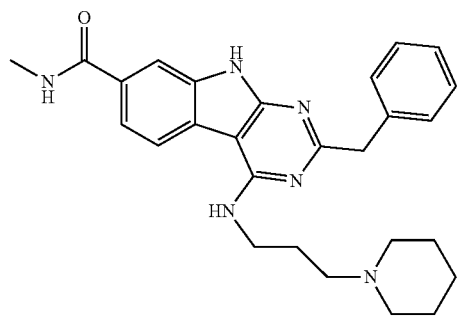
13
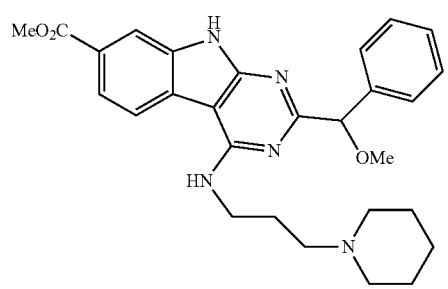
14
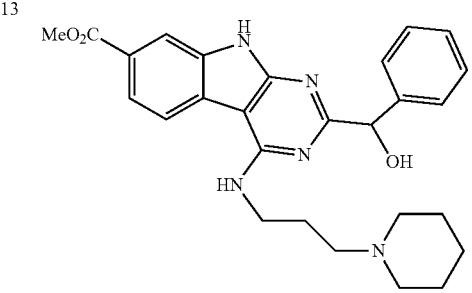

-continued
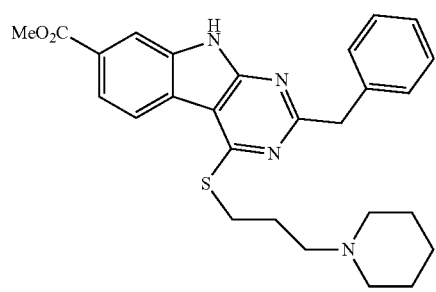
15
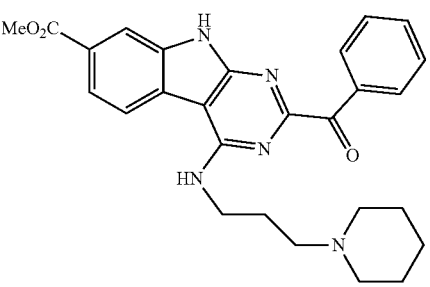
16
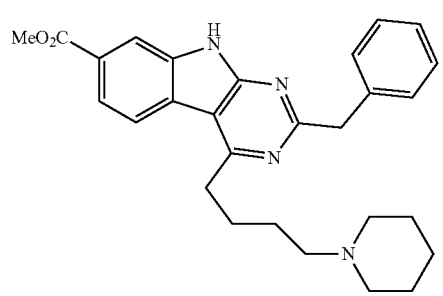
17
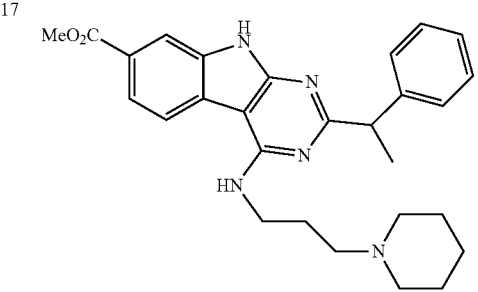
18
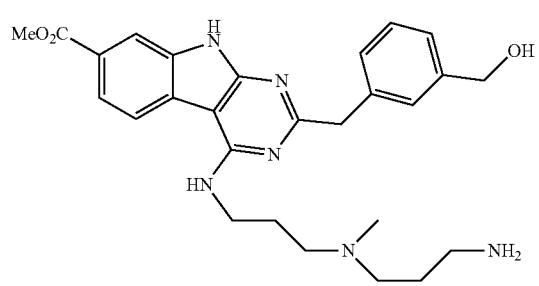
19
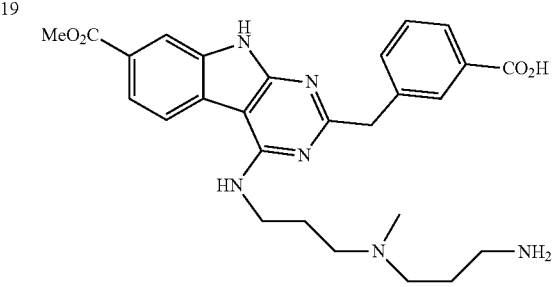
20
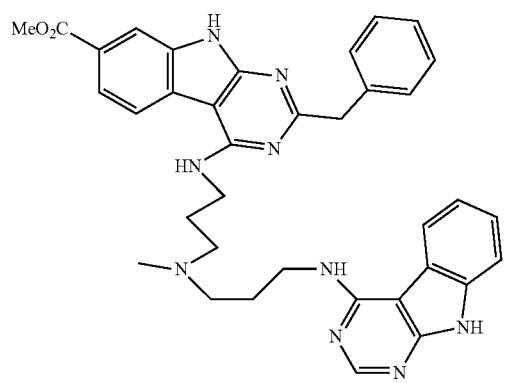
21
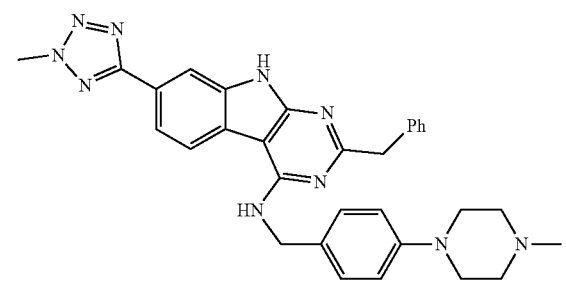
22
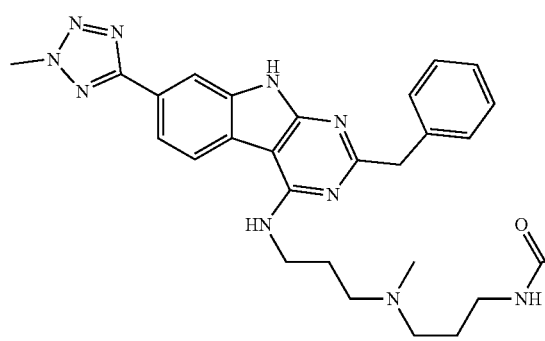
23

-continued
24
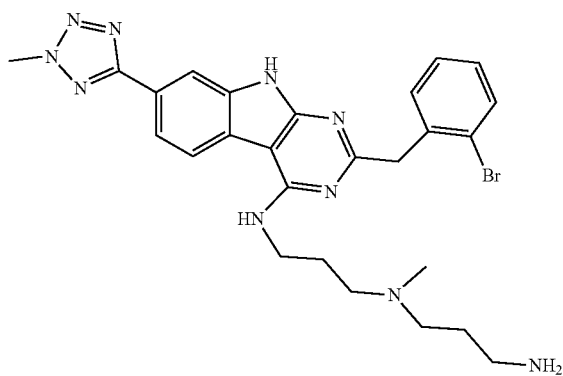
25
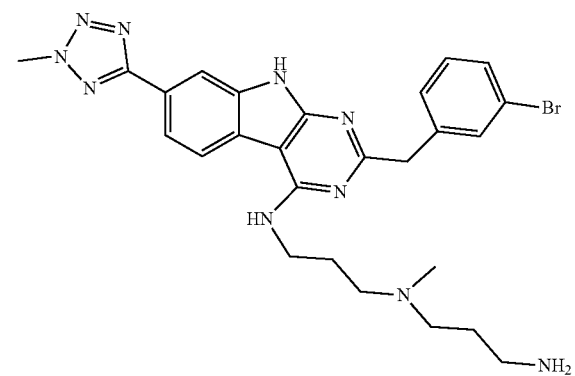
26
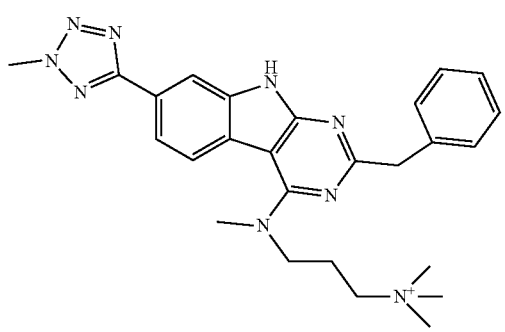
27
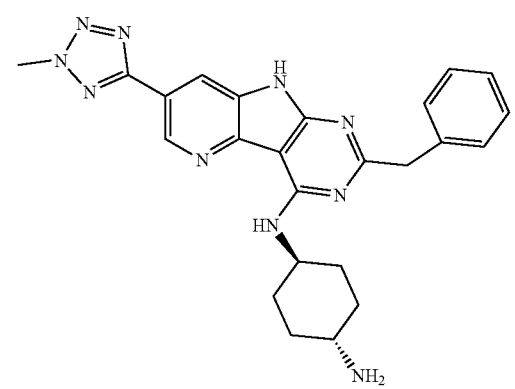
28
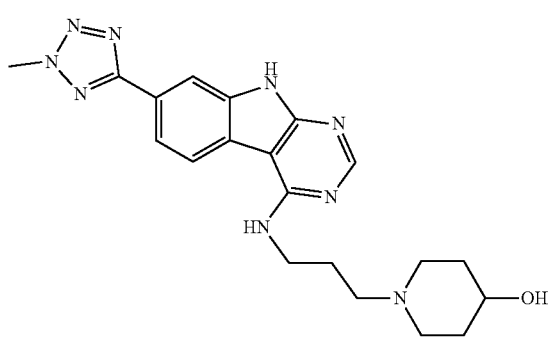
29
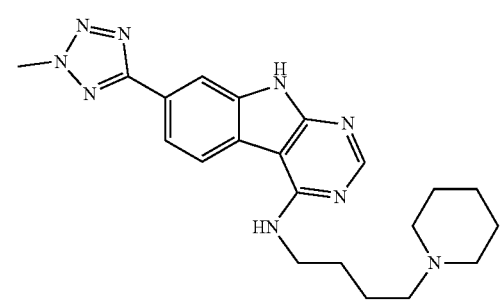
30
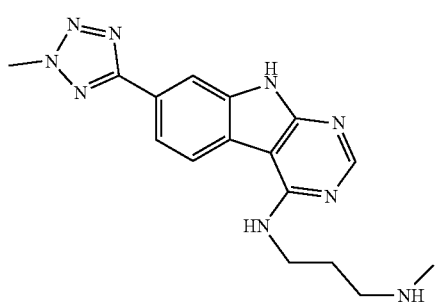
31
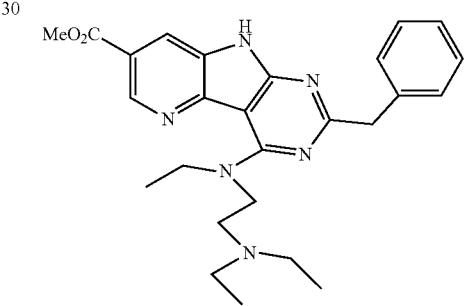

32
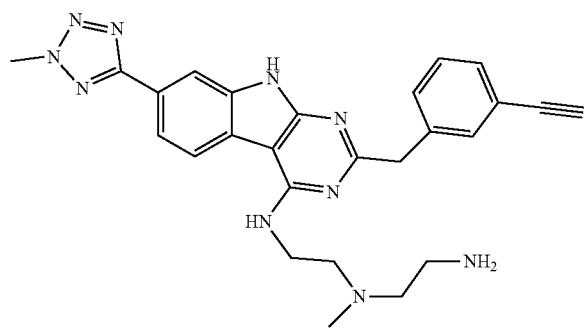
33
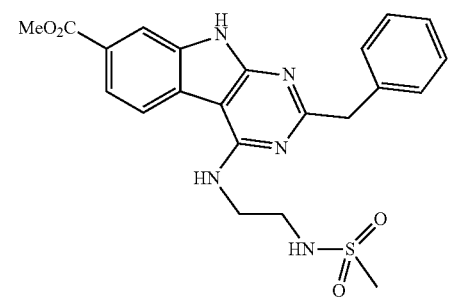
34
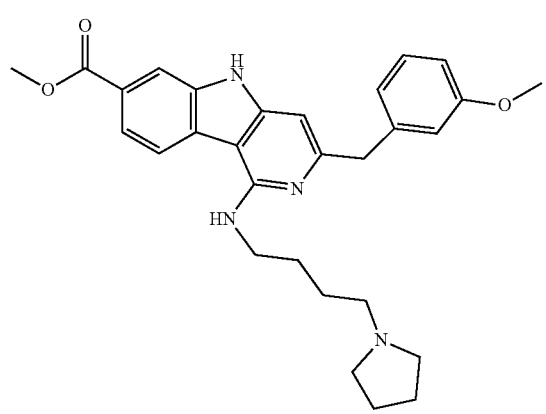
35
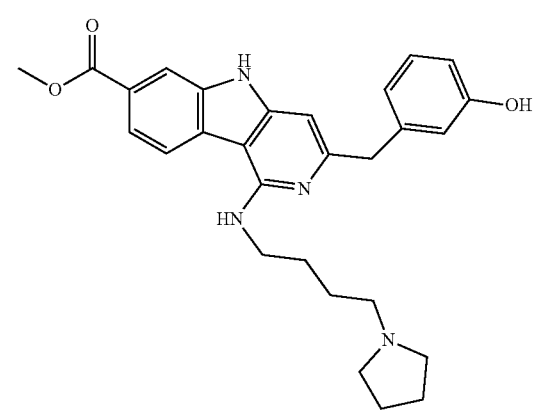
36
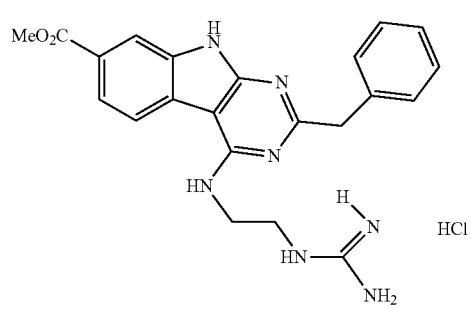
37
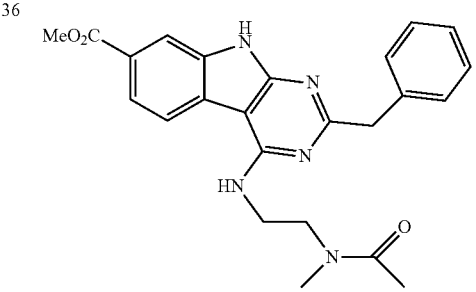
38
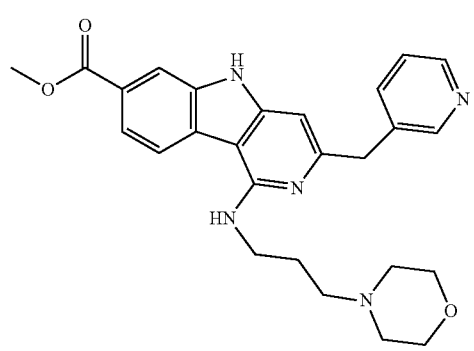
39
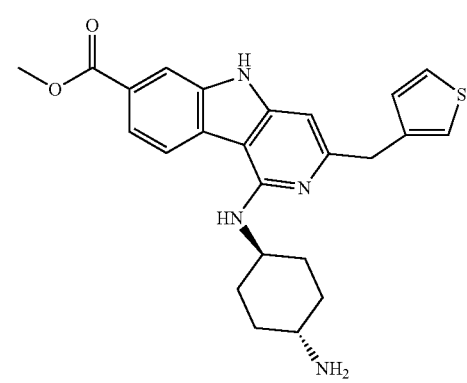

-continued
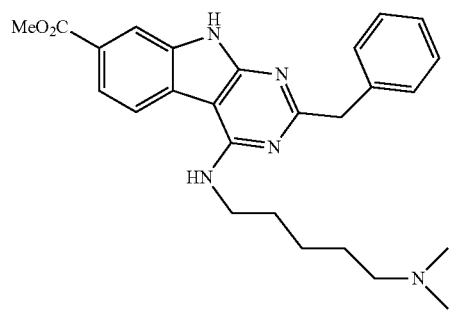
40
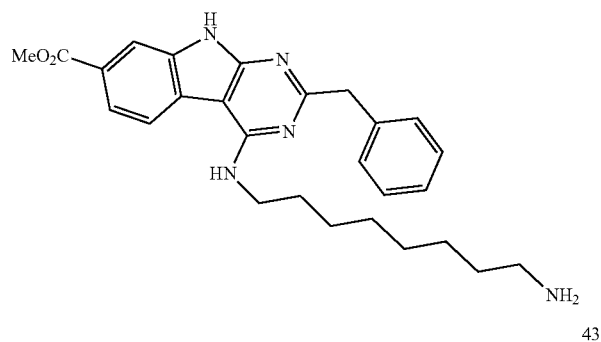
41
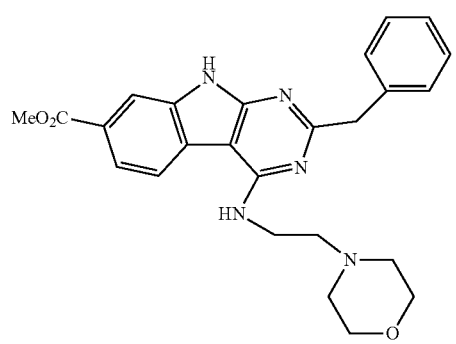
42
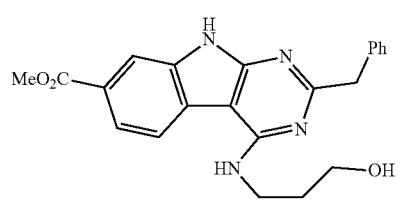
43
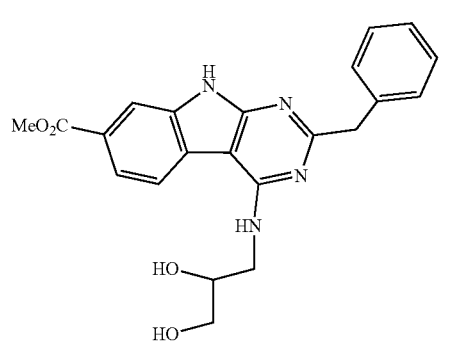
44
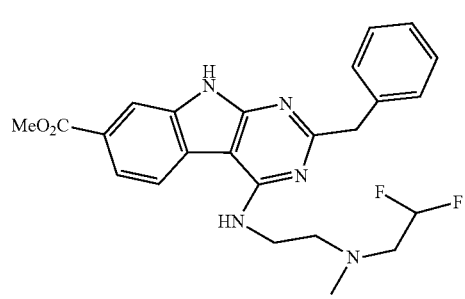
45
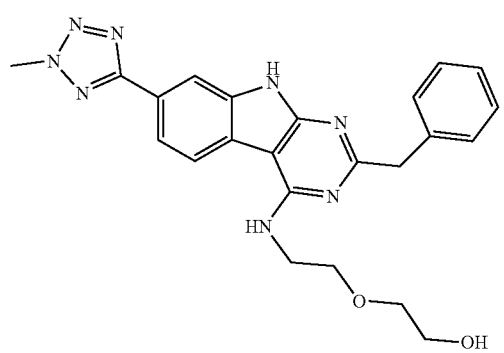
46
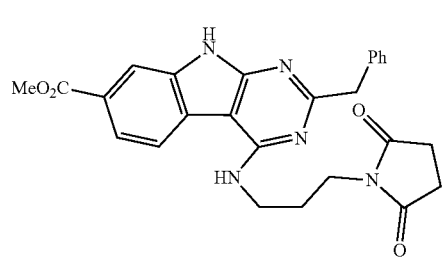
47
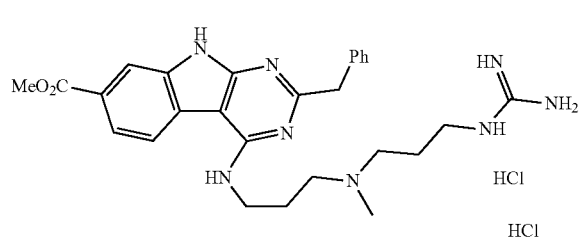
48
49

| 50 | 51 |
|---|---|
| 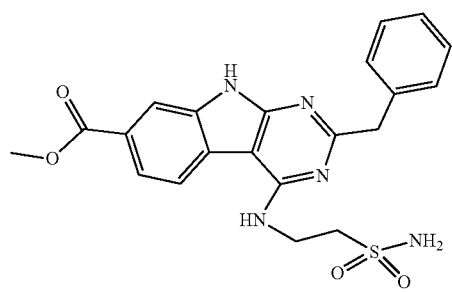 | 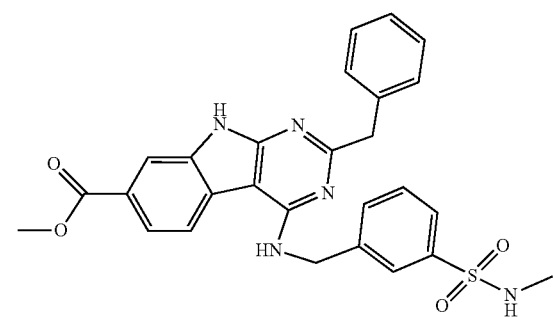 |
| 52 | 53 |
| 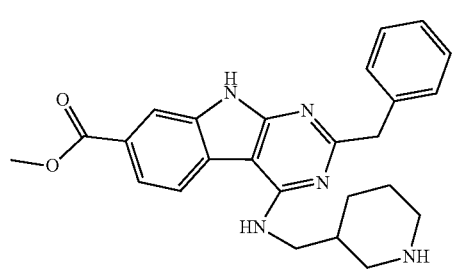 | 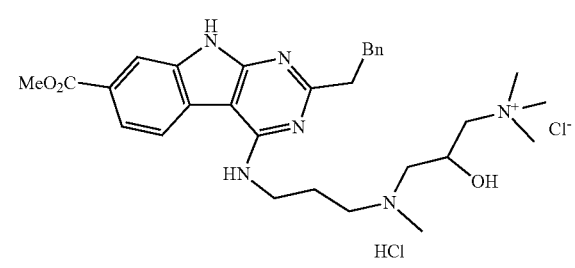 |
| 54 | 55 |
| 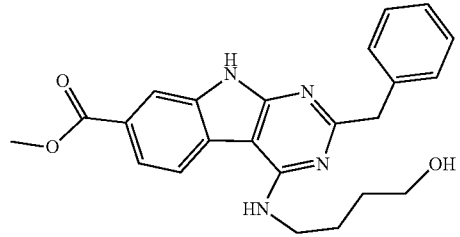 | 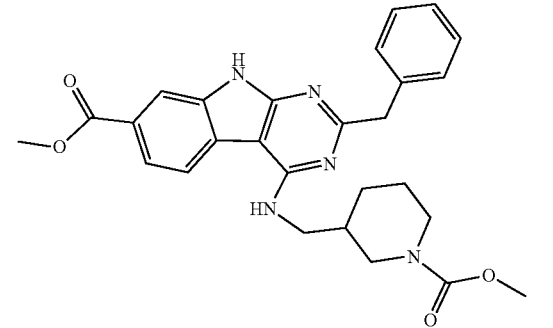 |
| 56 | |
| 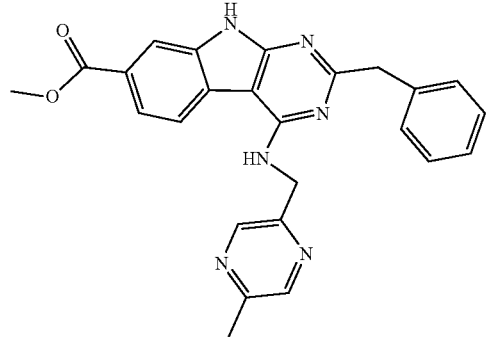 | |
| 58 | 59 |
| 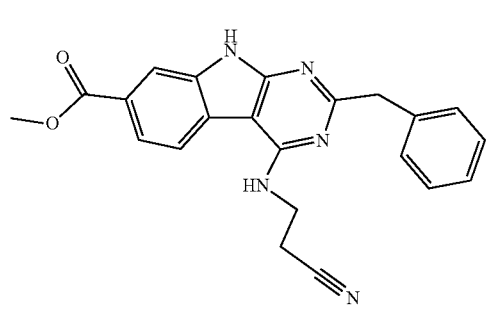 | 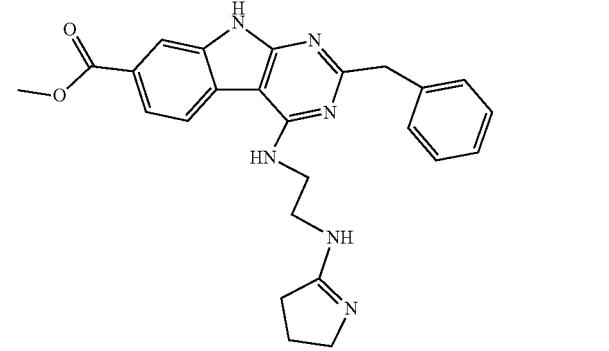 |

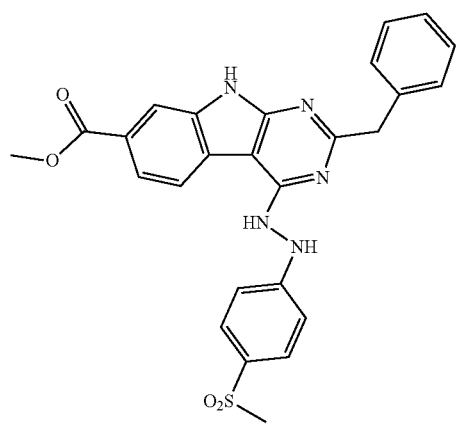

60

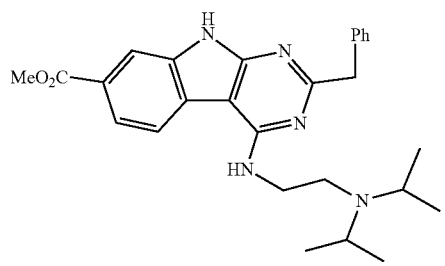

61 or a pharmaceutically acceptable salt thereof.

13. The method of claim 1, further controlling an inflammatory state in said patient.

14. The method of claim 1, wherein the graft comprises a dendritic cell population and mast cells.

15. The method of claim 1, wherein the graft comprises FCER1$^+$CD34$^+$ cells, CD34$^+$CD45RA$^+$ cells, CD34$^+$CD86$^+$ cells, CD34$^+$CD45RA$^-$ cells and CD34$^-$ cells.

* * * * *